(12) United States Patent
Kim et al.

(10) Patent No.: US 10,406,184 B2
(45) Date of Patent: Sep. 10, 2019

(54) METHOD OF TREATING AN INFLAMMATORY DISEASE USING LACTIC ACID BACTERIA-DERIVED EXTRACELLULAR VESICLES

(71) Applicant: MD HEALTHCARE INC., Seoul (KR)

(72) Inventors: Yoon-Keun Kim, Namyangju-si (KR); Bok Yang Pyun, Seoul (KR); Minhye Kim, Seoul (KR); Jun-Pyo Choi, Seoul (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

(21) Appl. No.: 15/556,953

(22) PCT Filed: Mar. 11, 2016

(86) PCT No.: PCT/KR2016/002473
§ 371 (c)(1),
(2) Date: Sep. 8, 2017

(87) PCT Pub. No.: WO2016/144139
PCT Pub. Date: Sep. 15, 2016

(65) Prior Publication Data
US 2018/0055894 A1    Mar. 1, 2018

(30) Foreign Application Priority Data

Mar. 11, 2015  (KR) .................. 10-2015-0033698
Mar. 10, 2016  (KR) .................. 10-2016-0029069

(51) Int. Cl.
| *A61K 35/747* | (2015.01) |
| *A61K 8/99* | (2017.01) |
| *A61K 9/00* | (2006.01) |
| *A61Q 19/00* | (2006.01) |
| *C12Q 1/689* | (2018.01) |
| *A61K 35/744* | (2015.01) |
| *G01N 33/50* | (2006.01) |
| *A61P 11/00* | (2006.01) |
| *A61P 29/00* | (2006.01) |
| *A61P 17/00* | (2006.01) |
| *A61P 11/06* | (2006.01) |
| *A61P 11/02* | (2006.01) |

(52) U.S. Cl.
CPC .............. *A61K 35/747* (2013.01); *A61K 8/99* (2013.01); *A61K 9/007* (2013.01); *A61K 35/744* (2013.01); *A61P 11/00* (2018.01); *A61P 11/02* (2018.01); *A61P 11/06* (2018.01); *A61P 17/00* (2018.01); *A61P 29/00* (2018.01); *A61Q 19/00* (2013.01); *C12Q 1/689* (2013.01); *G01N 33/50* (2013.01); *C12Q 2600/118* (2013.01)

(58) Field of Classification Search
None
See application file for complete search history.

(56) References Cited

U.S. PATENT DOCUMENTS

| 8,969,653 B2 * | 3/2015 | Gho ..................... C12Q 1/6883 424/234.1 |
| 9,066,971 B2 * | 6/2015 | Gho ..................... A61K 9/5068 |
| 2018/0057896 A1 * | 3/2018 | Kim ........................ A61K 35/74 |

FOREIGN PATENT DOCUMENTS

| JP | 2010-47504 A | 3/2010 |
| JP | 2010/047504 | * 4/2010 |
| KR | 10-2005-0109928 A | 11/2005 |
| KR | 10-2011-0025603 A | 3/2011 |
| KR | 10-2011-0082481 A | 7/2011 |
| KR | 10-2013-0034764 A | 4/2013 |

OTHER PUBLICATIONS

Van Bergenhenegouwen J. et al. Extracellular Vesicles Modulate Host Microbe Responses by Altering TLR2 Activity and Phagocytosis. Plos One 9(2)1-11, Feb. 2014. (Year: 2014).*
Kim M. et al. Lactobacillus Plantarum Derived Extracellular Vesicles . . . Allergy Asthma Immunology Research 10(5)516-532, Sep. 2018. (Year: 2018).*
Van Niel, G. et al. Shedding Light on the Cell Biology of Extracellular Vesicles. Nature Reviews/Molecular Biology 19:213-228, Apr. 2018. (Year: 2018).*
Aydin M. et al. Reversing the Progress of Liver Fibrosis Using Membrane Vesicles Secreted from Commensal Bacteria. J of Hepatology 60(1, Suppl. 1)S270, Apr. 2014. (Year: 2014).*

* cited by examiner

*Primary Examiner* — Ralph J Gitomer
(74) *Attorney, Agent, or Firm* — Vorys, Sater, Seymour & Pease LLP; Mih Suhn Koh

(57) ABSTRACT

Provided is a composition for preventing, ameliorating, or treating inflammatory diseases, the composition including, as active ingredients, lactic acid bacteria-derived extracellular vesicles isolated from culture fluid of lactic acid bacteria; and a method for diagnosing atopic dermatitis. The composition including the lactic acid bacteria-derived extracellular vesicles as active ingredients is expected to be usefully used in development of drugs, cosmetics, or health functional food for preventing, ameliorating, or treating inflammatory diseases such as atopic dermatitis, chronic rhinitis, chronic rhinosinusitis, asthma, chronic obstructive pulmonary disease, sepsis, etc. Also, the composition will be usefully used for diagnosis of atopic dermatitis by measuring the distribution of lactic acid bacteria-derived extracellular vesicles in a urine or blood sample.

1 Claim, 28 Drawing Sheets
Specification includes a Sequence Listing.

| Group | Mouse (n=5) | lactic acid bacteria EV | causative factor |
|---|---|---|---|
| 1 | SKH-1 | - | - |
| 2 | SKH-1 |  | S. aureus EV (10 μg) |
| 3 | SKH-1 | CJLP133 EV (1 μg) | S. aureus EV (10 μg) |
| 4 | SKH-1 | CJLP133 EV (10 μg) | S. aureus EV (10 μg) |
| 5 | SKH-1 | CJLP133 EV (100 μg) | S. aureus EV (10 μg) |
| 6 | SKH-1 | Dexamethasone (300 μg) (i.p. injection) | S. aureus EV (10 μg) |

FIG. 31

S. aureus EV (10 μg, Skin patch)

↓ ↓ ↓ ↓ ↓ ↓ ↓ ↓ ↓ ↓ ↓

Day  1  3  5  8  10  12  15  17  19  21  24  26  28
     ↑  ↑  ↑  ↑  ↑   ↑   ↑   ↑   ↑   ↑   ↑   ↑

CJLP133 EV (Oral administration)    evaluation

| Group | Mouse (n=5) | lactic acid bacteria EV | causative factor |
|---|---|---|---|
| 1 | SKH-1 | - | - |
| 2 | SKH-1 |  | S. aureus EV (10 μg) |
| 3 | SKH-1 | CJLP133 EV (1 μg) | S. aureus EV (10 μg) |
| 4 | SKH-1 | CJLP133 EV (10 μg) | S. aureus EV (10 μg) |
| 5 | SKH-1 | CJLP133 EV (100 μg) | S. aureus EV (10 μg) |
| 6 | SKH-1 | Dexamethasone (300 μg) (i.p. injection) | S. aureus EV (10 μg) |

| Group | Mouse (n=5) | lactic acid bacteria EV |
|---|---|---|
| 1 | Balb/c | - |
| 2 | Balb/c | CJLP133 EV (500 μg) |

METHOD OF TREATING AN INFLAMMATORY DISEASE USING LACTIC ACID BACTERIA-DERIVED EXTRACELLULAR VESICLES

STATEMENT REGARDING GOVERNMENT RIGHTS

This research was supported by a grant of the Korea Health technology R&D Project through the Korea Health Industry Development Institute (KHIDI), funded by the Ministry of Health & Welfare, Republic of Korea. (Grant Number: HI13C0040).

CROSS-REFERENCE TO RELATED APPLICATION

This application claims priority to and the benefit of Korean Patent Application No. 10-2015-0033698 filed on Mar. 11, 2015, Korean Patent Application No. 10-2016-0029069 filed on Mar. 10, 2016 and International Patent Application No. PCT/KR2016/002473, filed on Mar. 11, 2016, the disclosure of which is incorporated herein by reference in its entirety.

SEQUENCE LISTING

The Sequence Listing submitted in text format (.txt) filed on Sep. 8, 2017, named "SequenceListing.txt", created on Sep. 5, 2017, 836 bytes), is incorporated herein by reference.

TECHNICAL FIELD

The present invention relates to a composition for preventing, improving or treating an inflammatory disease, comprising lactic acid bacteria-derived extracellular vesicles as active ingredients, and a method for diagnosing atopic dermatitis.

BACKGROUND ART

In recent years, disease patterns have changed from acute infectious diseases to chronic inflammatory diseases because of a change in life style. Inflammation is a defense mechanism occurring in the body in response to external toxic substances entering the body. Acute inflammation is triggered by short-term infection of environmental bacteria, fungi, etc., and chronic inflammation is triggered when causative agents such as microorganisms, allergens, etc. that exist in the environment are continuously absorbed into the body. Recently, the importance of infectious causes for the occurrence of chronic inflammatory diseases that have been recognized to be triggered by noninfectious causes is being emphasized. As, representatively, helicobacter bacteria that have been known to co-exist in the stomach have been identified as a critical causative agent of gastritis, gastric cancer, etc., bacteria and substances derived from the bacteria, which are known to co-exist in the environment, have recently attracted attention as causative agents of cancer triggered by chronic inflammatory diseases and complications of chronic inflammation.

Atopic dermatitis is a type of dermal disease that is most frequently found in early-infancy and childhood, and the first signal of atopic march progressing to asthma or allergic rhinitis. In addition, atopic dermatitis is a chronic inflammatory disease characterized by chronic itching and repeated inflammation of the skin and thus physically and mentally affecting not only the patient himself but also the quality of life in the family. In recent years, the increase in global prevalence of the atopic dermatitis is being followed by an increasing attention thereto. In Korea, according to the International Study of Allergy and Asthma in Childhood (ISAAC) survey conducted by the Korean Pediatric Allergy Respiratory Society, for atopic dermatitis until now, compared to 1995, prevalence increased both at the ages ranging from 6 to 12 in 2000 (15.3% in 1995 and 17.0% in 2000) and at the ages ranging from 12 to 15 (7.2% in 1995 and 9.2% in 2000), and for atopic dermatitis in the last 12 months, prevalence increased both at the age ranging from 6 to 12 in 2000 (7.3% in 1995 and 10.7% in 2000), and at the ages ranging from 12 to 15 (3.9% in 1995 and 6.1% in 2000). An allergic disease such as atopic dermatitis is triggered by combined interaction between a genetic factor and an environmental factor, and the recent growth trend is insufficient to be explained only by the genetic factor. Although differences in incidence of allergic diseases depending on a country reflects differences among ethnic groups, that is, the significance of genetic factors, the same result as shown by a surge of allergic diseases in the former East German region after reunification indicates that environmental factors are also significant. Such a surge of allergic diseases is involved in westernized life, and there may be three possible causes: first, an increase in exposure to house dust mites because of generally spending more time indoors, secondly, exposure to a wide range of microorganisms due to environmental hygiene and use of antibiotics, and thirdly, westernized eating habits.

Atopic dermatitis patients frequently have dermal infection caused by functional disorder of a skin barrier, or immune dysfunction. Particularly, bacterial infections by *Staphylococcus*, viral infections by herpes simplex viruses, and fungal infections are common. Among these, *Staphylococcus aureus* is detected in 90% of patients with atopic dermatitis and is also detected in skin lesions without obvious infection symptoms, and the toxin of *Staphylococcus aureus* serves as a superantigen that increases allergic immune responses, which is known to exacerbate skin itching and lesions.

The prognosis of atopic dermatitis varies depending on a patient's skin condition, stimulation factor, accompanying allergic disease, and bacterial infection. Generally, atopic dermatitis tends to improve with an increasing age, while symptoms are severe at the young age and chronic lesions persist. However, some reports show that about 40% of patients have improved symptoms at the age of around 5, and the reason for this improvement is controversial. The most representative method for treating atopic dermatitis when exacerbated due to various reasons includes elimination of the causative agents and simultaneous application of topical and systemic steroids or topical immunosuppressants as well as proper use of moisturizers. However, recent studies suggest that, in addition to these factors, lactic acid bacteria or a culture thereof may be used to lower the severity of atopic dermatitis.

Asthma and chronic obstructive pulmonary disease (COPD) are diseases characterized by airway obstruction due to chronic airway inflammation, wherein the asthma is characterized by reversible airway obstruction, and the COPD is characterized by irreversible airway obstruction. A hypersensitivity reaction to allergens derived from house dust mites as a causative factor of asthma is known to be important in the pathogenesis of eosinophilic asthma, and in recent years, research has been focused on the importance of bacteria-derived substances for neutrophilic inflammation, which is a characteristic pathological feature of severe asthma or COPD. Particularly, the finding that extracellular vesicles derived from pathogenic bacteria present in indoor dust are important in the onset of asthma and COPD has been reported. In addition, it has been reported that bacteria and substances derived from the bacteria co-existing in the nasal cavity play an important role in the pathogenesis of chronic rhinosinusitis, and the reduction of the diversity of bacterial flora in the nasal cavity and the increase in specific pathogens, particularly, Staphylococci, are important in the onset of chronic rhinosinusitis.

Bacteria secrete bilayer-structured lipoproteins, that is, extracellular vesicles (EVs) frequently called nanovesicles into an extracellular environment. Gram-negative bacteria-derived extracellular vesicles, or outer membrane vesicles (OMVs) contain a toxic protein and bacterial DNA and RNA as well as lipopolysaccharides, and gram-positive bacteria-derived extracellular vesicles also contain bacterial cell wall ingredients, such as peptidoglycan and lipoteichoic acid as well as a toxic protein and nucleic acid. In recent years, it has been reported that EVs secreted from the representative gram-positive bacteria *Staphylococcus aureus* are important causative agents of atopic dermatitis, chronic rhinosinusitis, neutrophilic asthma and COPD, and it has been reported that large amounts of EVs derived from pathogenic gram-negative bacteria such as *Pseudomonas aeruginosa* and *Acinetobacter bacumannii* are present in indoor dust, and are important causative agents of asthma, COPD, and lung cancer when inhaled.

Meanwhile, metagenomics also called environmental genomics may be analysis of metagenome materials obtained from environmental samples. Recently, the bacterial composition of human microbial flora can be cataloged by a method based on a 16S ribosome RNA (16S rRNA) base sequence, and 16S rRNA is sequenced using the 454FLX titanium platform. In the meantime, while research has been conducted on metagenomes analyzed from patient samples, it was not known that bacteria-derived EVs are present in serum or urine, and therefore metagenomic analysis was not conducted on bacteria-derived EVs isolated from serum or urine. In addition, on the basis of results of metagenomic analysis using DNA of EVs isolated from patients' sera or urine, there is no case that bacteria-derived EVs are used to prevent or treat an inflammatory disease such as atopic dermatitis, asthma, COPD, chronic rhinitis, chronic rhinosinusitis, and sepsis.

DISCLOSURE

Technical Problem

As a result of metagenomic analysis performed using DNA of EVs isolated from the urine of a patient with atopic dermatitis and a normal person, the present inventors confirmed that lactic acid bacteria-derived EVs were significantly increased in the urine of the normal person compared to the patient with atopic dermatitis, and the lactic acid bacteria-derived EVs effectively inhibit inflammatory responses induced by EVs derived from *Staphylococcus aureus* (*S. aureus*) and *Pseudomonas aerugionsa* (*P. aeruginosa*), which are the main causative agents of an inflammatory disease, and thus the present invention was completed.

Therefore, the present invention is directed to providing a composition for preventing, improving or treating an inflammatory disease, comprising lactic acid bacteria-derived EVs as active ingredients.

The present invention is also directed to providing a method for diagnosing atopic dermatitis.

However, technical problems to be solved in the present invention are not limited to the above-described problems, and other problems which are not described herein will be fully understood by those of ordinary skill in the art from the following descriptions.

Technical Solution

In one aspect, the present invention provides a pharmaceutical composition for preventing or treating an inflammatory disease, comprising lactic acid bacteria-derived EVs as active ingredients.

In another aspect, the present invention provides a cosmetic composition for improving an inflammatory disease, comprising lactic acid bacteria-derived EVs as active ingredients.

In still another aspect, the present invention provides a health functional food composition for improving an inflammatory disease, comprising lactic acid bacteria-derived EVs as active ingredients.

In yet another aspect, the present invention provides an inhalant composition for preventing or treating an inflammatory disease, comprising lactic acid bacteria-derived EVs as active ingredients.

In an exemplary embodiment of the present invention, the lactic acid bacteria may include bacteria in the order Lactobacillales.

In another exemplary embodiment of the present invention, the bacteria in the order Lactobacillales may include bacteria in the genus *Lactococcus, Lactobacillus*, or *Leuconostoc*.

In still another exemplary embodiment of the present invention, the bacteria in the genus *Lactobacillus* may include *Lactobacillus plantarum*.

In yet another exemplary embodiment of the present invention, the EVs may have an average diameter of 10 to 300 nm.

In yet another exemplary embodiment of the present invention, the EVs may be isolated from a culture of lactic acid bacteria.

In yet another exemplary embodiment of the present invention, the EVs are naturally or artificially secreted from lactic acid bacteria.

In yet another exemplary embodiment of the present invention, the inflammatory disease may be a disease selected from the group consisting of atopic dermatitis, chronic rhinitis, chronic rhinosinusitis, asthma, COPD, and sepsis.

In yet another aspect, the present invention provides a method for diagnosing atopic dermatitis, comprising the following steps:

(a) extracting genes from EVs isolated from clinical samples;

(b) sequencing the genes; and (c) determining that there is a high risk of atopic dermatitis when distribution of lactic acid bacteria-derived EVs is lower than that of a normal person through the sequencing.

In one exemplary embodiment of the present invention, the gene may be DNA or RNA.

In another exemplary embodiment of the present invention, the clinical sample may be urine or blood.

In still another exemplary embodiment of the present invention, the sequencing may be performed through polymerase chain reaction (PCR).

In yet another aspect, the present invention provides a method for preventing or treating an inflammatory disease, which comprises administering a composition comprising lactic acid bacteria-derived EVs as active ingredients to a subject.

In yet another aspect, the present invention provides a use of lactic acid bacteria-derived EVs for preventing or treating an inflammatory disease.

In yet another aspect, the present invention provides a use of lactic acid bacteria-derived EVs for diagnosing atopic dermatitis.

Advantageous Effects

The inventors identified by in vitro and in vivo experiments that larger amounts of lactic acid bacteria-derived EVs are significantly distributed in a normal person compared to an atopic dermatitis patient, inflammation responses in epithelial cells and inflammatory cells due to exposure of Staphylococcus or Pseudomonas-derived EVs are effectively inhibited by the lactic acid bacteria-derived EVs, and a composition comprising the lactic acid bacteria-derived EVs as active ingredients to prevent, improve or treat an inflammatory disease such as atopic dermatitis, chronic rhinitis, chronic rhinosinusitis, asthma, chronic obstructive pulmonary disease or sepsis is expected to be useful in development of drugs, cosmetics, or health functional food.

Also, as distribution of lactic acid bacteria-derived EVs is detected in a urine or blood sample, the lactic acid bacteria-derived EVs can be useful for diagnosing atopic dermatitis.

DESCRIPTION OF DRAWINGS

FIG. 31 shows the protocol for evaluating therapeutic effects by oral administration of lactic acid bacteria-derived EVs (CJLP133 EV) to atopic dermatitis mouse models caused by *S. aureus*-derived EVs (*S. aureus* EV).

MODES OF THE INVENTION

Figure 1:
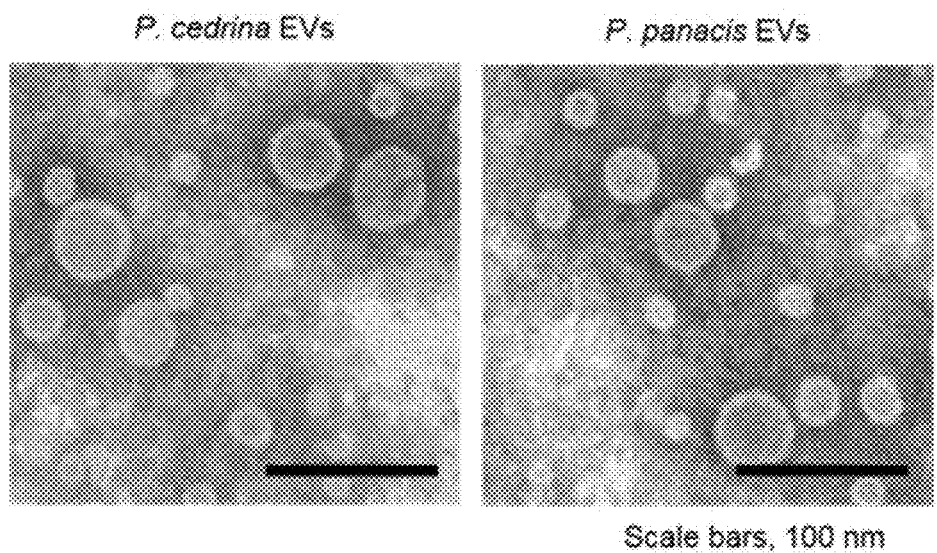
FIG. 1 shows *Pseudomonas cedrina* (*P. cedrina*) and *Pseudomonas panacis* (*P. panacis*)-derived EVs isolated from in vitro cultures of enterobacteria such as *P. cedrina* and *P. panacis*, obtained using an electron microscope, respectively.

As a result of metagenomic analysis using DNA of EVs isolated from the urine of an atopic dermatitis patient and a normal person, it was confirmed that, compared to the atopic dermatitis patient, lactic acid bacteria-derived EVs in the urine of the normal person are considerably increased, and the lactic acid bacteria-derived EVs efficiently inhibit inflammation responses induced by EVs derived from main causative factors of inflammatory diseases such as *S. aureus* (*S. aureus*) and *Pseudomonas aeruginosa* (*P. aeruginosa*), and thus the present invention was completed.

In one exemplary embodiment of the present invention, as a result of identifying distribution and excretion patterns by isolating EVs from enterobacteria such as *P. cedrina* and *P. panacis* in the bodies and orally administering the bacteria and the EVs derived therefrom to mice, it was confirmed that the enterobacteria are not absorbed in the whole body, whereas the enterobacteria-derived EVs are systematically absorbed and then excreted in urine (see Examples 1 and 2).

In another exemplary embodiment of the present invention, DNA of bacteria-derived EVs isolated from the urine and sera of atopic dermatitis patients are each subjected to metagenomic analysis at a bacteria phylum, class, order, family or genus level, and as a result, it was confirmed that distributions of bacteria-derived EVs in the urine and serum exactly match (see Example 3).

In still another exemplary embodiment of the present invention, based on the above result, metagenomic analysis was carried out using DNA of EVs isolated from the urine of atopic dermatitis patients and normal persons. As a result of analysis of EV distribution at each of the bacteria phylum, class, order, family, and genus levels, compared to the normal persons, EVs derived from bacteria in the genus *Alicyclobacillus*, the genus *Methylobacterium*, the order Streptophyta, the genus *Propionibacterium*, and the genus *Pseudomonas* are significantly increased, but EVs derived from bacteria the order Lactobacillales, the genus *Lactobacillus*, the genus *Leuconostoc*, and the genus *Lactococcus* are significantly decreased in the urine of the atopic dermatitis patients.

In yet another exemplary embodiment of the present invention, based on the metagenome result, as a result of analysis of the characteristics of EVs isolated after lactic acid bacteria such as *Lactobacillus plantarum* isolated from fermented food were in vitro cultured, spherical vesicles having an average diameter of approximately 15 nm were able to be isolated (see Example 5), and it was confirmed that, following the treatment of dermal epithelial cells and macrophages with the vesicles, inflammation responses induced by the treatment of EVs secreted from *S. aureus* and *P. aeruginosa*, which are the main causative agents of inflammatory diseases, are significantly inhibited (see Examples 6 to 9).

In yet another exemplary embodiment of the present invention, based on the in vitro test result, it was confirmed that, when lactic acid bacteria-derived vesicles are orally or percutaneously administered to a atopic dermatitis mouse model induced by *S. aureus*-derived EVs, dermal inflammation caused by *S. aureus*-derived vesicles is effectively inhibited by lactic acid bacteria-derived vesicles (see Examples 10 and 11), and according to multiple oral administrations of high doses of lactic acid bacteria-derived EVs to mice, it was confirmed that there was no difference in various biomarkers from the control, resulting in verification of EV stability (see Example 12).

Thus, in one aspect, the present invention provides a pharmaceutical composition for preventing or treating an inflammatory disease, comprising lactic acid bacteria-derived EVs as active ingredients.

The term "inflammatory disease" used herein includes infectious inflammatory diseases induced by exposure to infectious factors such as bacteria or bacteria-derived vesicles, toxins, viruses, or fungi, allergens, allergic inflammatory diseases induced by exposure to allergens, and autoimmune inflammatory diseases caused by self-antigens.

The term "inflammatory disease" used herein is the generic term for inflammatory diseases caused by infectious factors, such as atopic dermatitis, chronic rhinitis, chronic rhinosinusitis, asthma, chronic obstructive pulmonary disease (COPD), and sepsis.

The term "allergic inflammatory disease" used herein is the generic term for inflammatory diseases caused by allergens, such as atopic dermatitis, chronic rhinitis, chronic rhinosinusitis, asthma, and chronic obstructive pulmonary disease (COPD).

The term "atopic dermatitis" used herein is the generic term for dermal diseases accompanying itching chronically occurring on the skin.

The term "prevention" used herein refers to all actions of inhibiting or delaying inflammatory diseases by administration of the pharmaceutical composition according to the present invention.

The term "treatment" used herein refers to all actions involved in alleviating or beneficially changing symptoms of inflammatory diseases by administration of the pharmaceutical composition according to the present invention.

The lactic acid bacteria of the present invention may include bacteria in the order Lactobacillales, the genus *Lactococcus*, the genus *Lactobacillus*, or the genus *Leuconostoc*, but the present invention is not limited thereto.

The bacteria in the genus *Lactobacillus* preferably include *Lactobacillus plantarum*, but the present invention is not limited thereto.

The EVs of the present invention may be isolated from a culture of the lactic acid bacteria or food fermented with the lactic acid bacteria, and may be naturally or artificially secreted from the lactic acid bacteria, but the present invention is not limited thereto.

A method for isolating EVs from a culture of the lactic acid bacteria of the present invention or fermented food is not particularly limited as long as the culture or fermented food contains EVs. For example, EVs may be isolated using centrifugation, ultracentrifugation, filtration using a filter, gel filtration chromatography, free-flow electrophoresis, capillary electrophoresis or a combination thereof, and the method may further include washing for removing impurities, and concentration of the obtained EVs.

The EVs isolated by the method of the present invention may have an average diameter of 10 to 300 nm, and preferably 10 to 200 nm, but the present invention is not limited thereto.

The pharmaceutical composition according to the present invention comprises lactic acid bacteria-derived EVs as active ingredients, and a pharmaceutically acceptable carrier. The pharmaceutically acceptable carrier is conventionally used for preparation, and may be, but is not limited to, a saline solution, distilled water, Ringer's solution, buffered saline, a cyclodextrin solution, a dextrose solution, a maltodextrin solution, glycerol, ethanol, or liposomes, etc., and may further include another conventional additive such as an antioxidant or a buffer as needed. In addition, the pharmaceutically acceptable carrier may be prepared as injectable forms such as an aqueous solution, a suspension, and an emulsion, pills, capsules, granules or tablets by further adding diluents, dispersants, surfactants, binders, lubricants, etc. Suitable pharmaceutically acceptable carriers and their preparations may be prepared according to each ingredient using a method disclosed in the Remington's Pharmaceutical Science. The pharmaceutical composition of the present invention is not limited to dosage forms, and thus may be prepared as injections, inhalants, topical formulations for skin, or oral medication.

The pharmaceutical composition of the present invention may be administered orally or parenterally (e.g., intravenously, subcutaneously, percutaneously, nasally, or intratracheally) according to a desired method, and a dose of the pharmaceutical composition of the present invention may be selected according to a patient's condition and body weight, severity of a disease, a dosage form, an administration route and duration by those of ordinary skill in the art.

The pharmaceutical composition of the present invention is administered at a pharmaceutically effective amount. In the present invention, the "pharmaceutically effective amount" refers to an amount sufficient to treat the disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The pharmaceutical composition of the present invention may be administered separately or in combination with other therapeutic agents, and may be sequentially or simultaneously administered with a conventional therapeutic agent, or administered in a single dose or multiple doses. In consideration of all of the above-mentioned parameters, it is important to achieve the maximum effect with the minimum dose without a side effect, and such a dose may be easily determined by one of ordinary skill in the art.

Specifically, the effective amount of the compound according to the present invention may vary depending on a patient's age, sex, and body weight, and may be generally administered at 0.001 to 150 mg and, preferably, 0.01 to 100 mg/kg of body weight daily or every other day, or once to three times a day. However, the effective amount may vary depending on an administration route, the severity of obesity, sex, body weight or age, and therefore, the scope of the present invention is not limited by the dose by any means.

In another aspect, the present invention provides a cosmetic composition for improving inflammatory diseases, comprising lactic acid bacteria-derived EVs as active ingredients.

The cosmetic composition of the present invention may comprise ingredients conventionally used in the cosmetic composition, for example, conventional additives including an antioxidant, a stabilizer, a solubilizer, a vitamin, a pigment and a flavoring, and a carrier, as well as lactic acid bacteria-derived EVs.

In addition, the composition of the present invention may be used in combination with an organic sunblock that has been conventionally used so long as the skin protection effect is not impaired, in addition to lactic acid bacteria-derived EVs. The organic sunblock may include at least one selected from the group consisting of glyceryl PABA, drometrizole trisiloxane, drometrizole, digalloyl trioleate, disodium phenyl dibenzimidazole tetrasulfonate, diethylhexyl butamido triazone, diethylamino hydroxybenzoyl hexyl benzoate, DEA-methoxycinnamate, a Lawson/dihydroxyacetone mixture, methylene bis-benzotriazolyl tetramethylbutyphenol, 4-methylbenzylidene camphor, menthyl anthranilate, benzophenone-3 (oxybenzone), benzophenone-4, benzophenone-8 (dixoyphebenzone), butyl methoxydibenzoylmethane, bisethylhexyloxyphenol methoxy phenyltriazine, cinoxate, ethyl dihydroxypropyl PABA, octocrylene, ethyl hexyldimethyl PABA, ethylhexyl methoxycinnamate, ethylhexyl salicylate, ethylhexyl triazone, isoamyl-p-methoxycinnamate, polysilicon-15 (dimethicodiethylbenzal malonate), terephthalylidene dicamphorsulfonic acid and a salt thereof, TEA-salicylate, and aminobenzoic acid (PABA).

Products that can contain the cosmetic composition of the present invention include, for example, cosmetics such as an astringent, a moisturizing lotion, a nourishing lotion, various creams, an essence, a mask pack, a foundation, etc., a cleanser, soap, a treatment, and other cosmetic liquids. Specific types of the cosmetic composition of the present invention include a skin lotion, a skin softener, a skin toner, an astringent, a lotion, a milk lotion, a moisturizer lotion, a nourishing lotion, a massage cream, a nourishing cream, a moisturizing cream, a hand cream, an essence, a nourishing essence, a pack, soap, a shampoo, a cleansing foam, a cleansing lotion, a cleansing cream, a body lotion, a body cleanser, an emulsion, a lipstick, a makeup base, a foundation, a pressed powder, a loose powder, and an eye shadow.

In still another aspect, the present invention provides a health functional food composition for improving an inflammatory disease, comprising lactic acid bacteria-derived EVs as active ingredients.

The term "improvement" used herein refers to all types of actions that at least reduce parameters related to a condition to be treated, for example, a degree of a symptom.

In the health functional food composition of the present invention, the active ingredient may be added alone to food or suitably used together with another food or other food ingredients according to a conventional method. A content of the active ingredient may be properly determined depending on the purpose of use (for prevention or improvement). Generally, in preparation of food or beverages, the composition of the present invention is added at 15 wt % or less, and preferably 10 wt % or less with respect to all ingredients. However, the content may be lower than the above ratio in the case of long-term absorption for the purpose of health and hygiene, or managing health.

The health functional food composition of the present invention contains any ingredient without particular limitation, in addition to the active ingredient as an essential ingredient in the above described ratio, and may contain a variety of flavoring agents or natural carbohydrates as additional ingredients like conventional beverages. Examples of the above-described natural carbohydrates include conventional sugars including monosaccharides such as glucose, fructose, etc.; disaccharides such as maltose, sucrose, etc.; and polysaccharides such as dextrin, cyclodextrin, etc., and sugar alcohols such as xylitol, sorbitol, erythritol, etc. Other than the above described flavoring agents, natural flavoring agents (thaumatin, stevia extracts (e.g., rebaudioside A, glycyrrhizin, etc.)) and synthetic flavoring agents (saccharin, aspartame, etc.) may be preferably used as a flavoring agent. A ratio of the natural carbohydrate may be suitably determined by the choice of one of ordinary skill in the art.

In addition to the above ingredients, the health functional food composition of the present invention may contain a variety of nutrients, vitamins, minerals (electrolytes), flavoring agents including synthetic and natural flavoring agents, coloring agents and fillers (cheese, chocolate, etc.), pectic acid and a salt thereof, alginic acid and a salt thereof, an organic acid, a protective colloid thickening agent, a pH regulator, a stabilizer, a preservative, glycerin, alcohol, or a carbonating agent used for soft drinks. Such ingredients may be used alone or in combination. Ratios of such additives may also be suitably selected by one of ordinary skill in the art.

In yet another aspect, the present invention provides an inhalant composition for preventing or treating an inflammatory disease, comprising lactic acid bacteria-derived EVs as active ingredients.

In the inhalant composition of the present invention, the active ingredient may be directly added to an inhalant or used in combination with other ingredients according to a conventional method. A content of the active ingredient may be suitably determined depending on the purpose of use (for prevention or treatment).

In yet another aspect, the present invention provides a method for diagnosing atopic dermatitis, which includes: extracting genes from EVs isolated from clinical samples; sequencing the genes; and determining that a risk of atopic dermatitis will be high when distribution of lactic acid bacteria-derived EVs is lower than a normal person through the sequencing.

The gene may be DNA or RNA, but the present invention is not limited thereto.

The clinical sample may be urine or blood, but the present invention is not limited thereto.

The sequencing may be performed by polymerase chain reaction (PCR), but the present invention is not limited thereto.

In yet another aspect of the present invention, the present invention provides a method for preventing or treating an inflammatory disease, which includes administering a composition comprising lactic acid bacteria-derived EVs as active ingredients to a subject.

The "subject" used herein refers to a target with a disease to be treated, more specifically a human, or a mammal such as a non-human primate, a mouse, a rat, a dog, a cat, a horse or a cow.

Hereinafter, exemplary examples will be provided to help in understanding of the present invention. However, the following examples are merely provided to more easily understand the present invention, but the scope of the present invention is not limited to the following examples.

EXAMPLES

Example 1. Isolation of EVs Derived from Entrobacteria and Characteristic Evaluation EVs were isolated from enterobacteria strains such as *P. cedrina* and *P. panacis*, and to analyze their characteristics, the two strains were cultured in Luria-Bertani broth (LB broth) at 30° C. and 25° C., respectively. Each bacterial culture was centrifuged at 5,000 g for 30 minutes twice to filter a supernatant using a 0.45 μm bottle-top filter (Corning), and then an eluted sample was concentrated using QuixStand™ (GE Healthcare Bio-Sciences AB). The concentrated sample was filtered once again using a 0.22 μm bottle-top filter (Corning) to isolate EVs, and a protein concentration of EVs was measured using a BCA assay (Thermo Scientific).

To observe the EVs isolated from the bacterial culture using an electron microscope, EVs in normal saline (PBS, 50 μg/ml) were placed on 300-mesh copper grids (Electron Microscopy Sciences), and stained with 2% uranyl acetate for 12 hours. Afterward, images were taken under an accelerating voltage of 100 kV using a JEM1011 microscope (JEOL) to observe the EVs.

Figure 2:
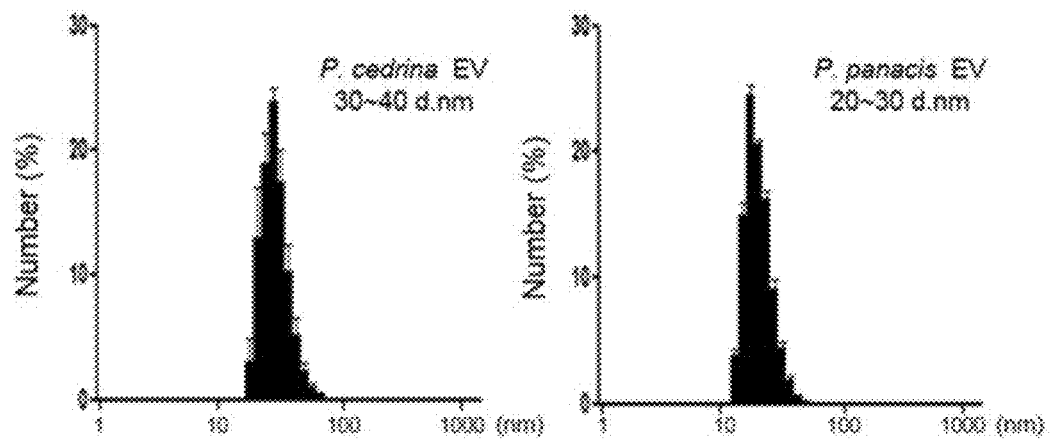
FIG. 2 shows sizes of *P. cedrina* and *P. panacis*-derived EVs, measured by dynamic light scattering.

As a result, as shown in FIG. 1, *P. cedrina* and *P. panacis*-derived EVs were observed to have spherical shapes. In addition, to measure sizes of EVs isolated from the bacterial culture by dynamic light scattering (DLS), diameters of EVs were measured using Zetasizer Nano S (Malvern Instruments Ltd., 633-nm laser line, scattered intensity 10×30 s). As a result, as shown in FIG. 2, diameters of the *P. cedrina* and *P. panacis*-derived EVs were measured at 30 to 40 nm and 20 to 30 nm, respectively.

Figure 3:
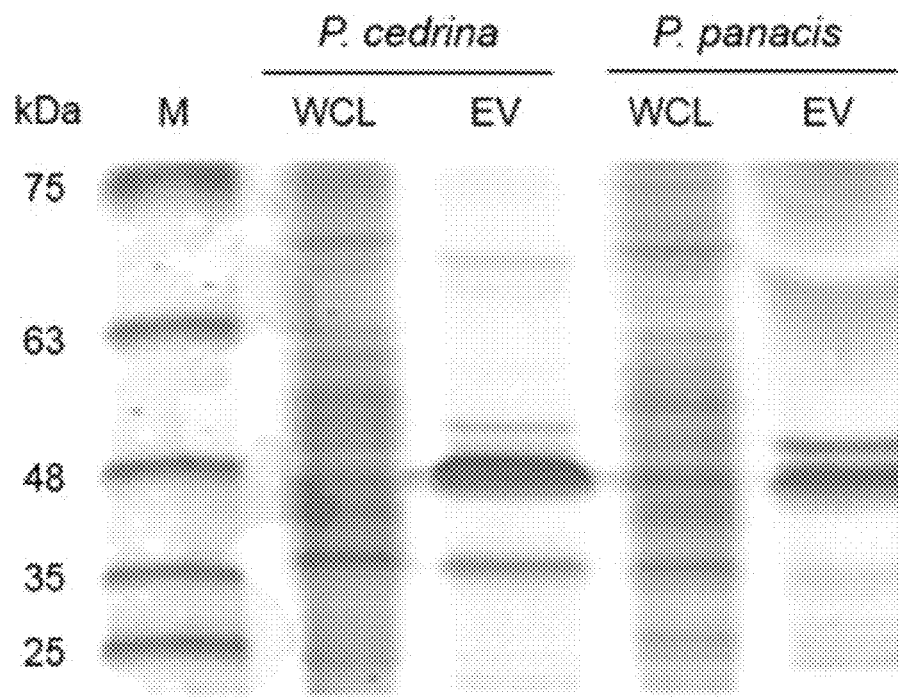
FIG. 3 shows CBB-R-250-stained gels obtained by SDS-PAGE to evaluate expression of proteins contained in *P. cedrina*, *P. panacis* and EVs derived therefrom.

Subsequently, to evaluate expressions of proteins contained in EVs derived from the two strains, sodium dodecyl sulfate polyacrylamide gel electrophoresis (SDS-PAGE) was carried out on protein samples. Whole-cell lysates (WCLs) obtained from the bacterial cells and the EVs derived from the bacteria (EV) were loaded in a 15% resolving gel, electrophoresis was performed, and then the gel in which the proteins are separated in sizes was stained with CBB R-250 (Coomassie Brilliant Blue R-250). As a result, as shown in FIG. 3, two strains of bacteria and the EVs derived therefrom showed different protein compositions.

Example 2. Evaluation of Absorption, Distribution, and Excretion of *P. cedrina* and *P. panacis*-Derived EVs To evaluate absorption, distribution and excretion after oral administration of *P. panacis* bacteria and *P. panacis*-derived EVs, experiments were carried out using C57BL/6J (6 to 8-wk-old) male mice provided from the Jackson Laboratory.

The *P. panacis* and EVs derived from the bacteria were labeled with Cy7 (GE Healthcare) for 1 hour at room temperature, and then the mice were fed a dose of 20 μg/mouse after overnight fasting. whole body images of the mice were taken at a wavelength of 780 to 800 nm using an IVIS spectrum CT (SelectScience) after 0 hr (h), 5 min (min), 3 hr (h), and 12 hr (h).

Figure 4:
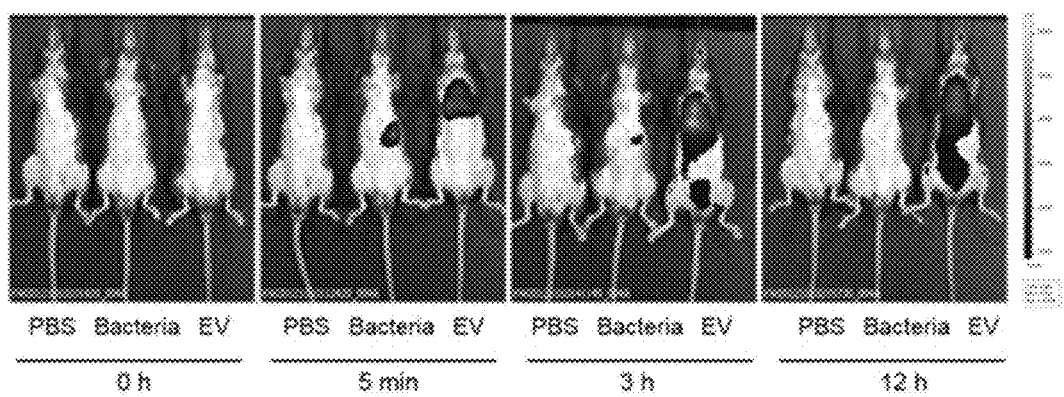
FIG. 4 shows whole body images illustrating distribution of bacteria and EVs in mice at a predetermined time after *P. panacis* and *P. panacis*-derived EVs are orally administered to the mice.
Figure 5:
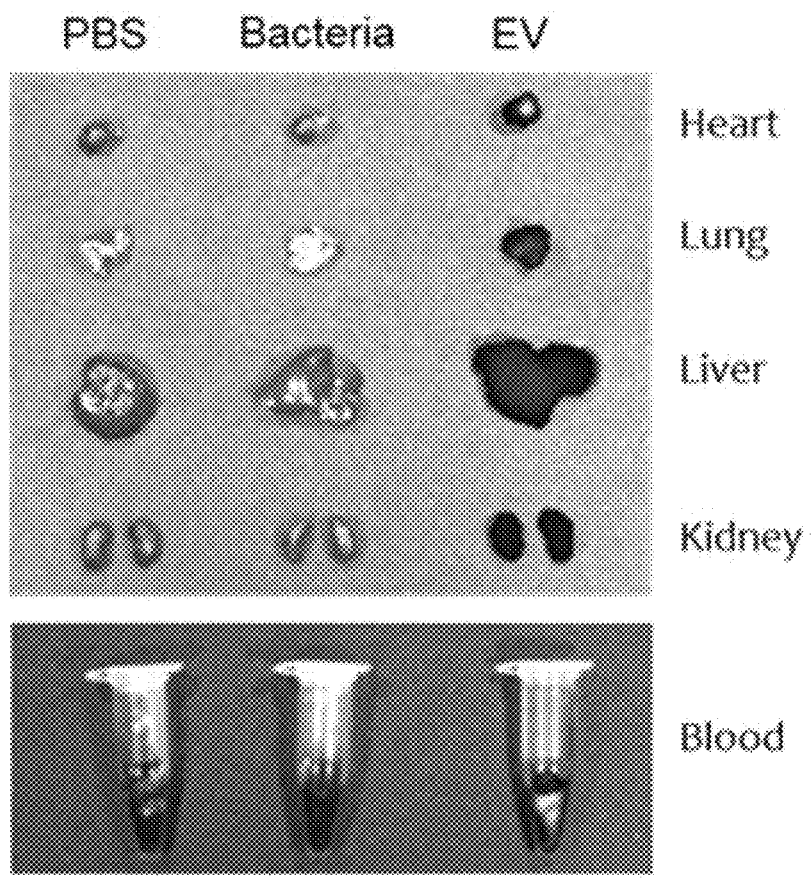
FIG. 5 shows bacterial and EV distribution extracted from the blood, heart, lungs, liver and kidneys of a mouse at 12 hours after oral administration of *P. panacis* and *P. panacis*-derived EVs thereto.

As a result, as shown in FIG. 4, *P. panacis* were found in the stomach 5 minutes after oral administration, and then excreted without being absorbed. However, it was confirmed that *P. panacis*-derived EVs (EV) were systemically absorbed 5 minutes after the oral administration, distributed into the cardiovascular system, the lungs, and the liver three hours after the administration, and excreted by the bladder. Afterward, to evaluate tissue distribution of the bacteria and the bacteria-derived EVs, the heart, the lungs, the liver and the kidneys were extracted at 12 hours after the oral administration, and fluorescent substances were detected using an IVIS spectrum CT. As a result, as shown in FIG. 5, in the blood, the heart, the lungs, the liver, and the kidneys, it was confirmed that the *P. panacis*-derived EVs were found and no *P. panacis* was found.

Further, to examine whether the bacteria-derived EVs were actually absorbed in the intestines by intestinal blood vessels, the large intestine was extracted from a mouse having undergone overnight fasting, and after sealing both ends thereof, the *P. panacis*-derived EVs labeled with 10 μg of GFP emitting green fluorescence were injected into the intestine. Afterward, an image of the blood of the lamina propria of the large intestine was taken using a TCS SP5 microscope (Leica).

Figure 6:
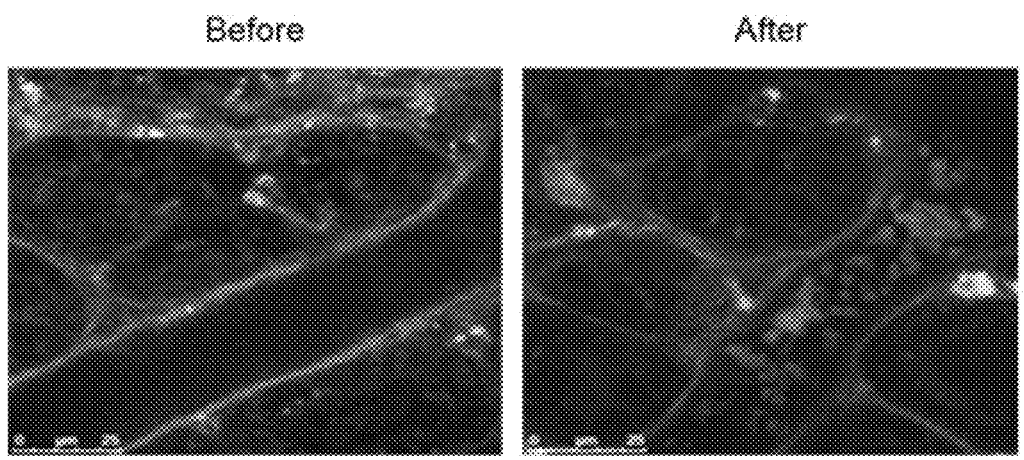
FIG. 6 shows that EVs are present in intestinal capillaries 10 minutes after *P. panacis*-derived EVs are directly administered to intestines.
Figure 7:
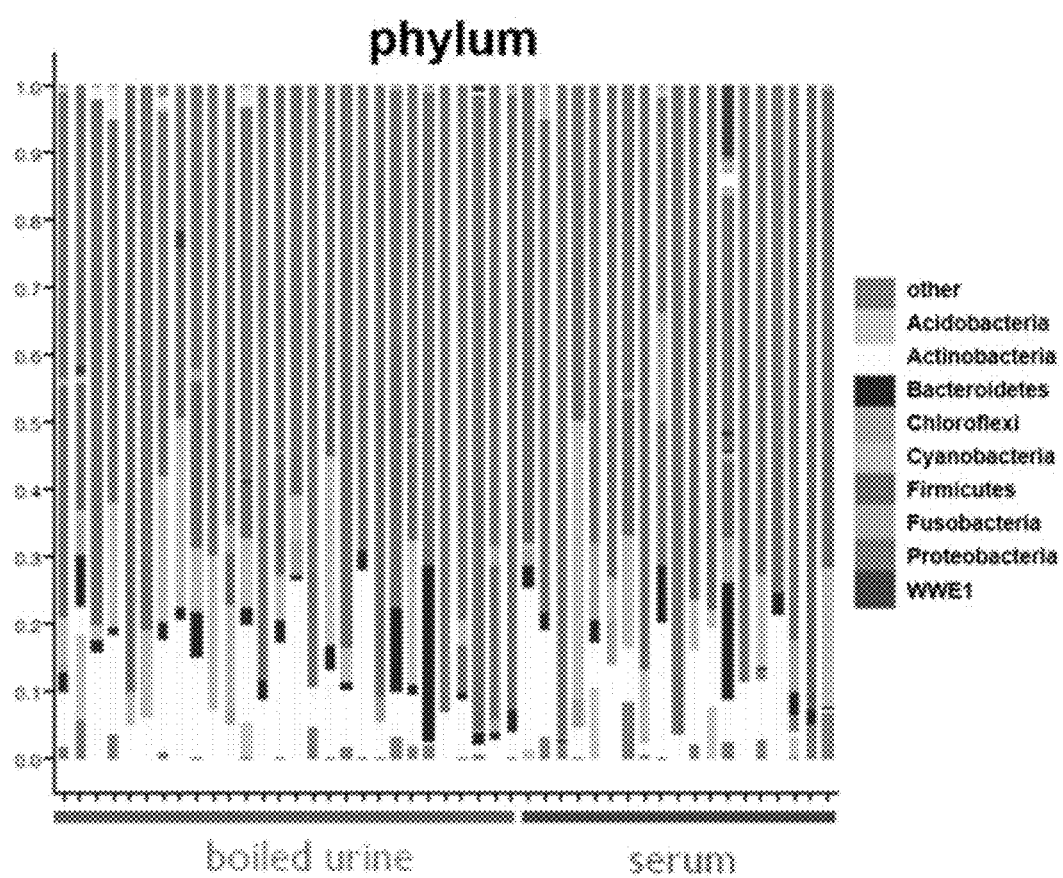
FIG. 7 shows the result of metagenomic analysis at a bacteria phylum level to compare distribution of bacteria-derived EVs isolated from the urine and sera of atopic dermatitis patients.
Figure 8:
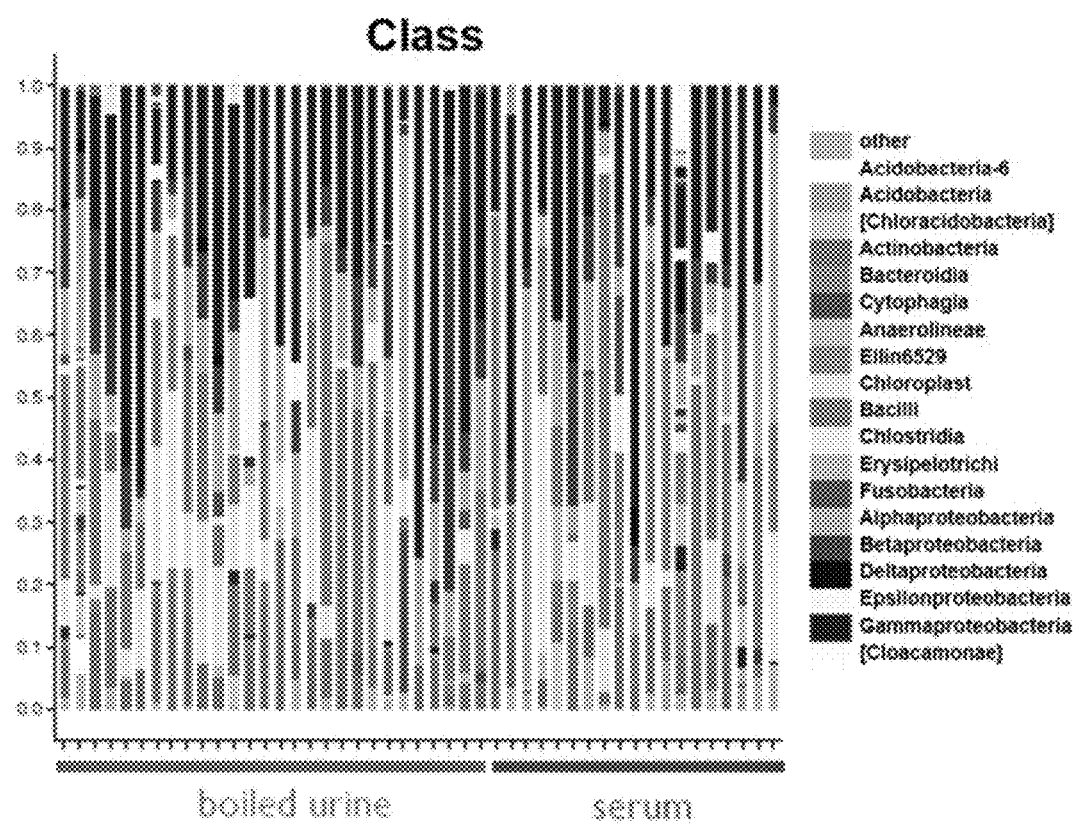
FIG. 8 shows the result of metagenomic analysis at a bacteria class level to compare distribution of bacteria-derived EVs isolated from the urine and sera of atopic dermatitis patients.
Figure 9:
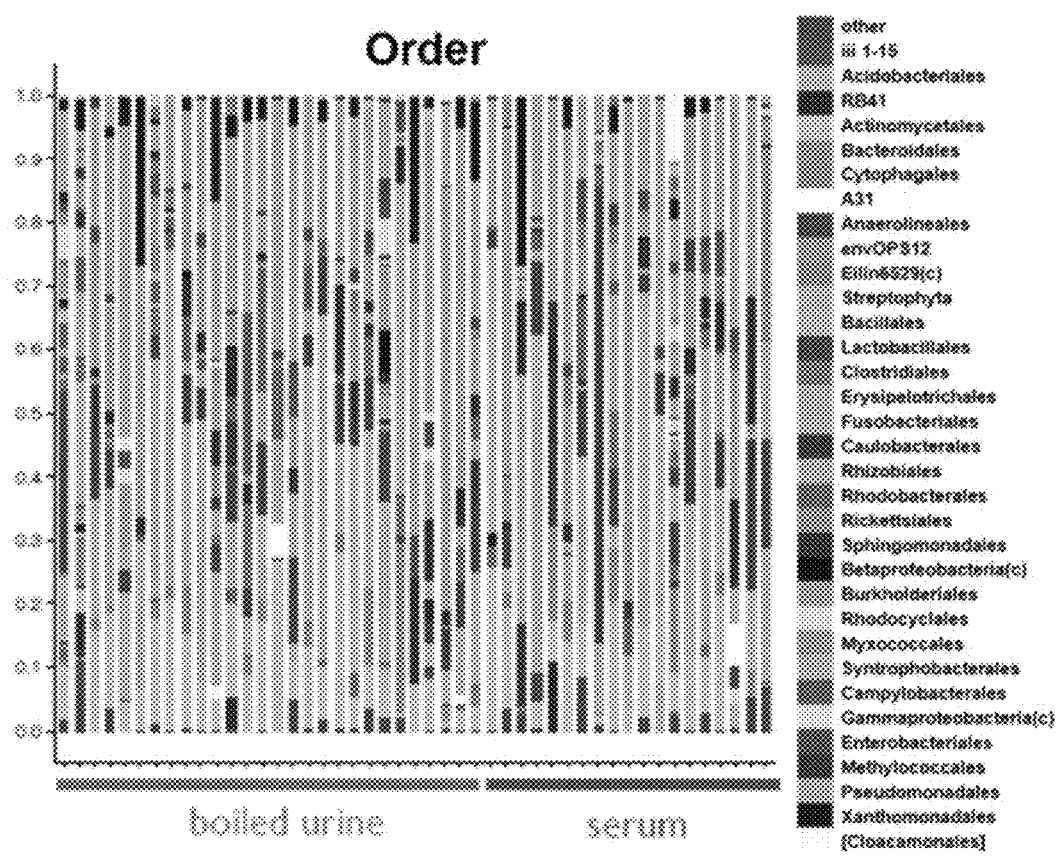
FIG. 9 shows the result of metagenomic analysis at a bacteria order level to compare distribution of bacteria-derived EVs isolated from the urine and sera of atopic dermatitis patients.
Figure 10:
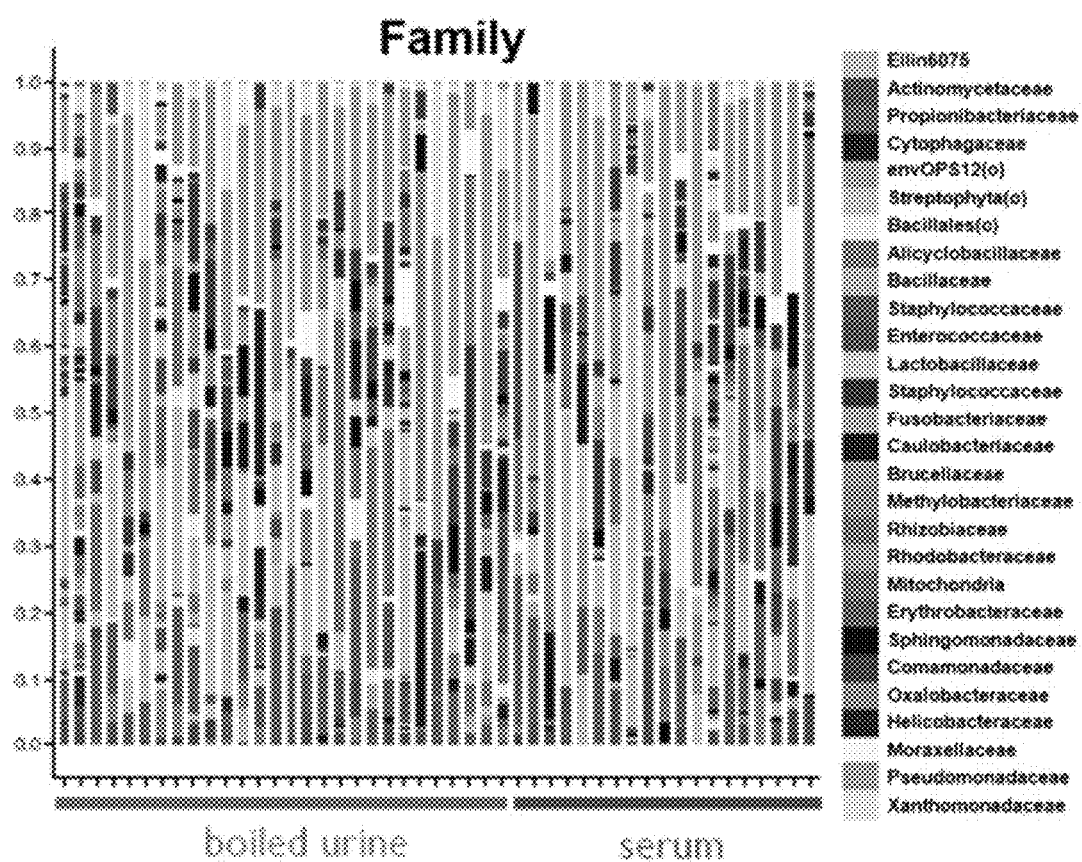
FIG. 10 shows the result of metagenomic analysis at a bacteria family level to compare distribution of bacteria-derived EVs isolated from the urine and sera of atopic dermatitis patients.
Figure 11:
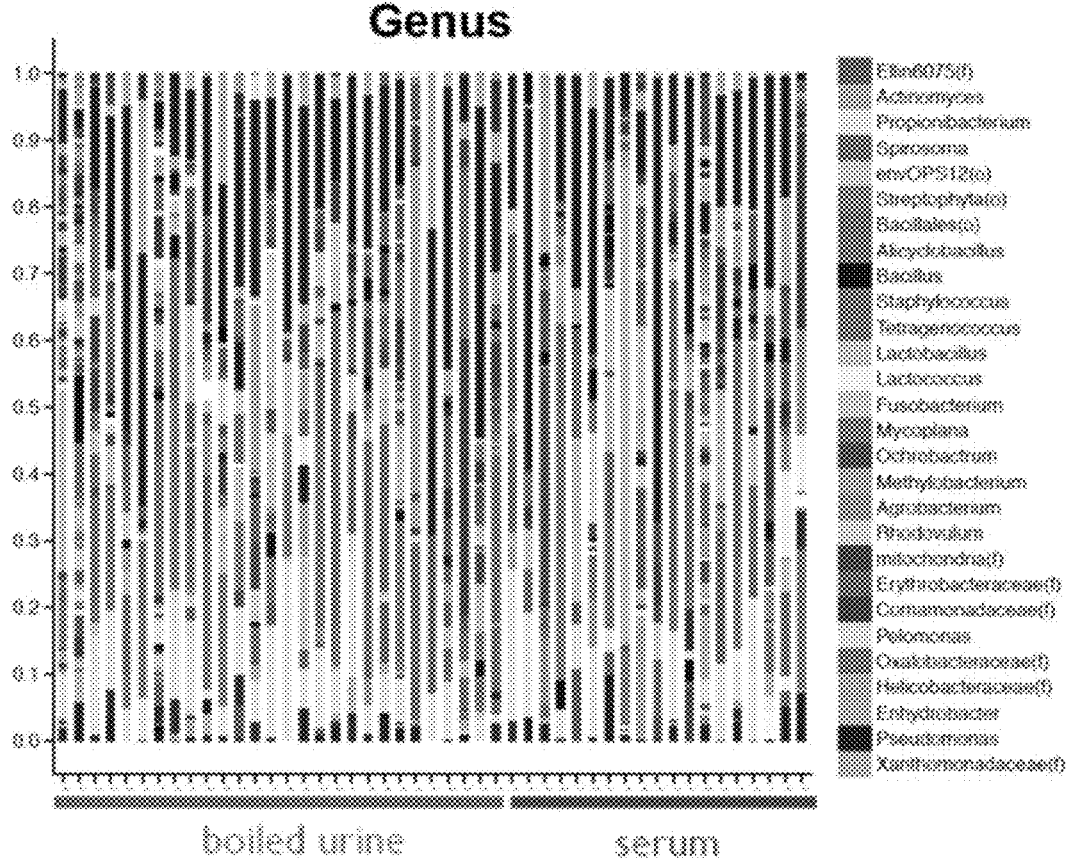
FIG. 11 shows the result of metagenomic analysis at a bacteria genus level to compare distribution of bacteria-derived EVs isolated from the urine and sera of atopic dermatitis patients.
Figure 12:
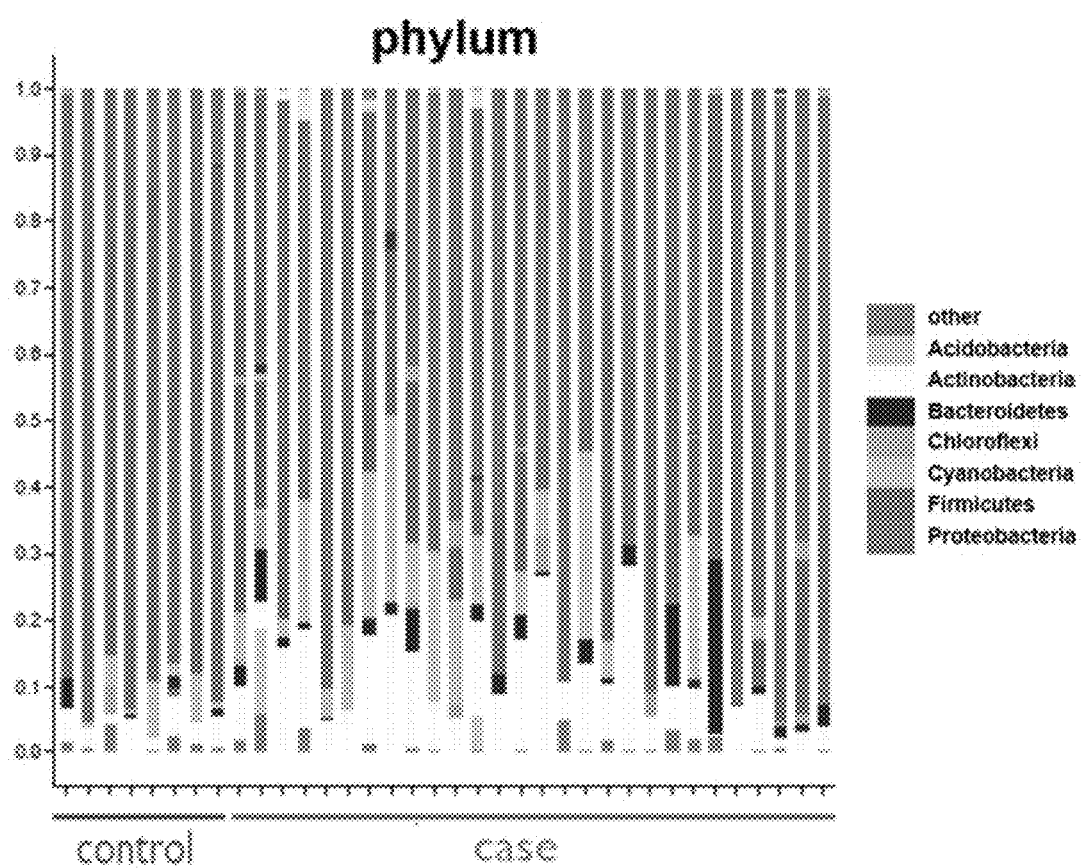
FIG. 12 shows the result of metagenomic analysis at a bacteria phylum level to compare distribution of bacteria-derived EVs isolated from the urine of an atopic dermatitis patient and a normal person.
Figure 13:
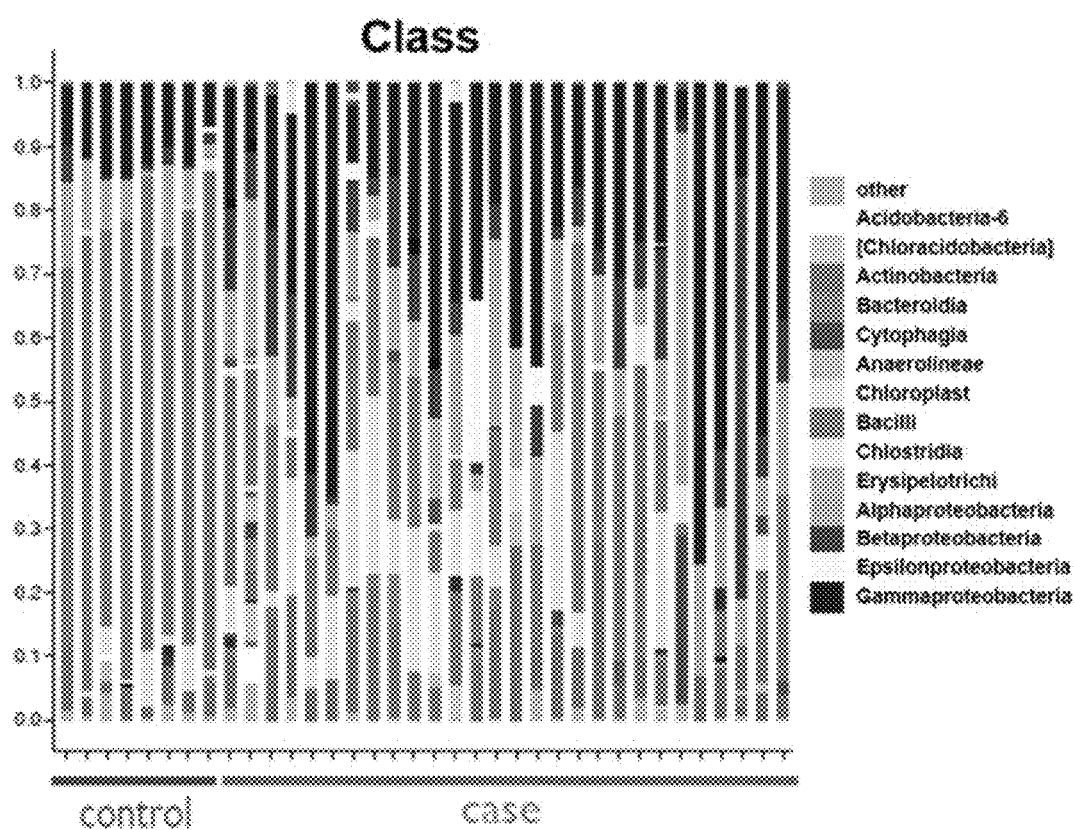
FIG. 13 shows the result of metagenomic analysis at a bacteria class level to compare distribution of bacteria-derived EVs isolated from the urine of an atopic dermatitis patient and a normal person.
Figure 14:
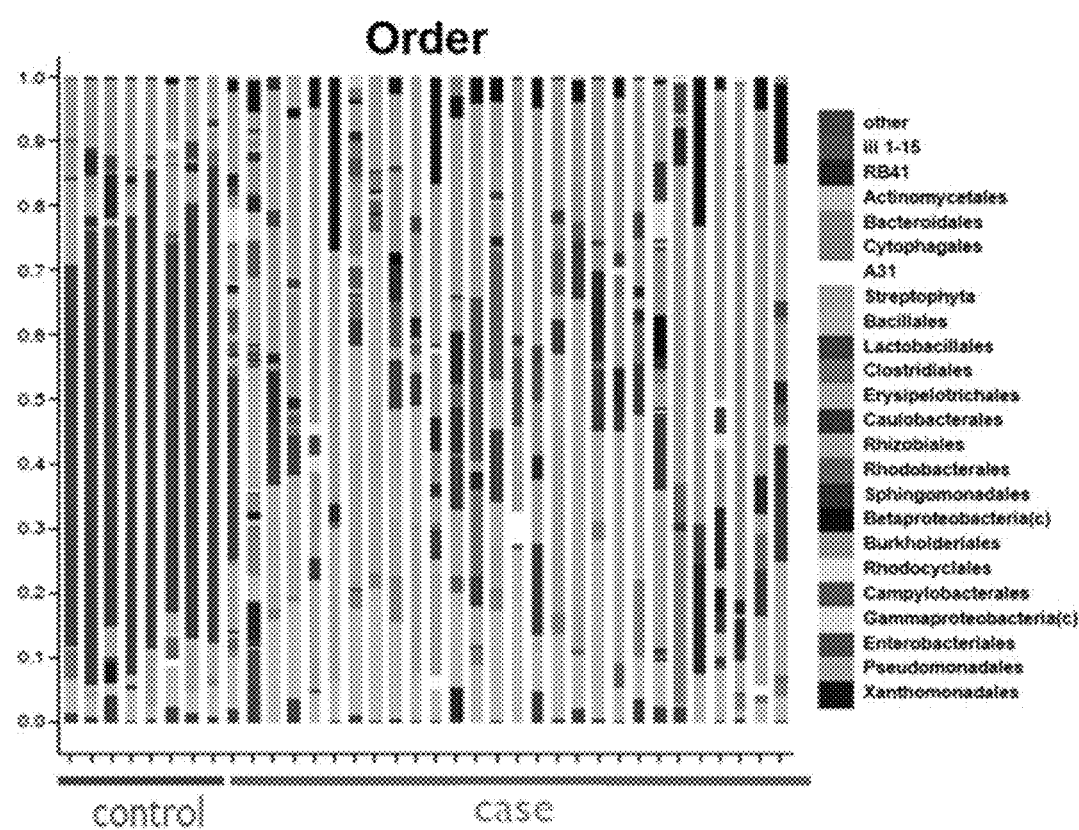
FIG. 14 shows the result of metagenomic analysis at a bacteria order level to compare distribution of bacteria-derived EVs isolated from the urine of an atopic dermatitis patient and a normal person.
Figure 15:
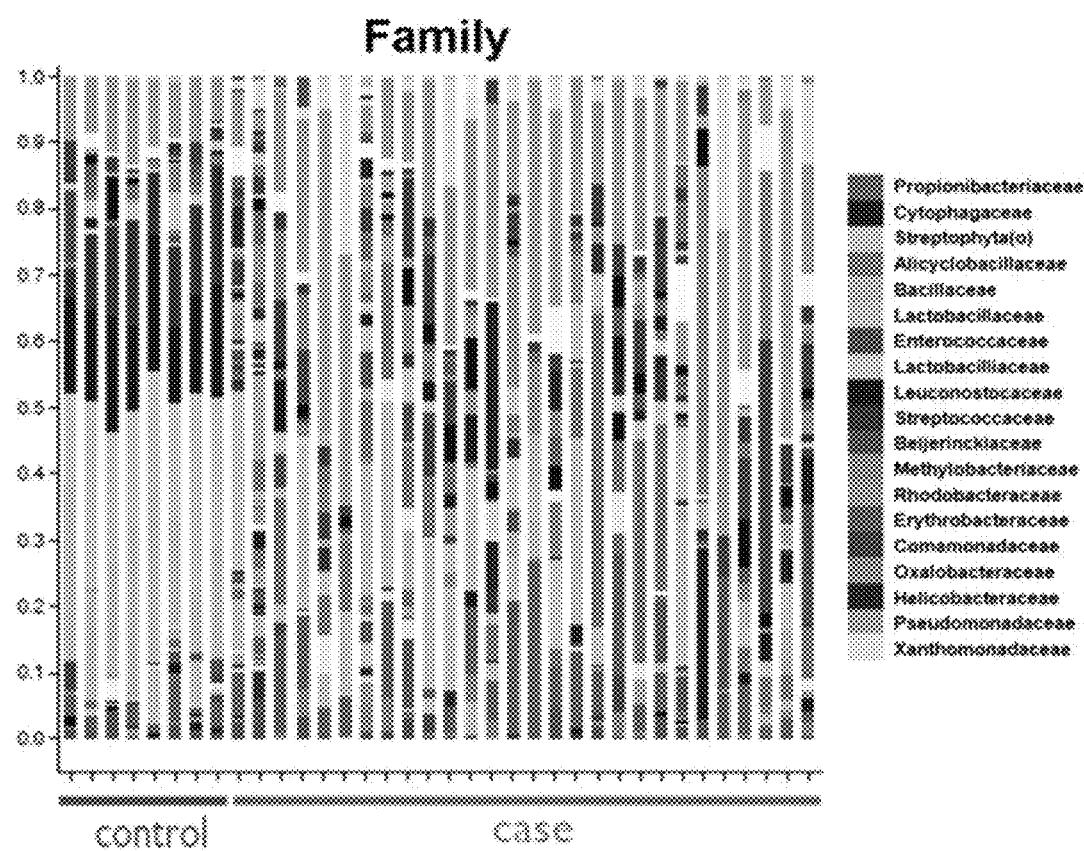
FIG. 15 shows the result of metagenomic analysis at a bacteria family level to compare distribution of bacteria-derived EVs isolated from the urine of an atopic dermatitis patient and a normal person.
Figure 16:
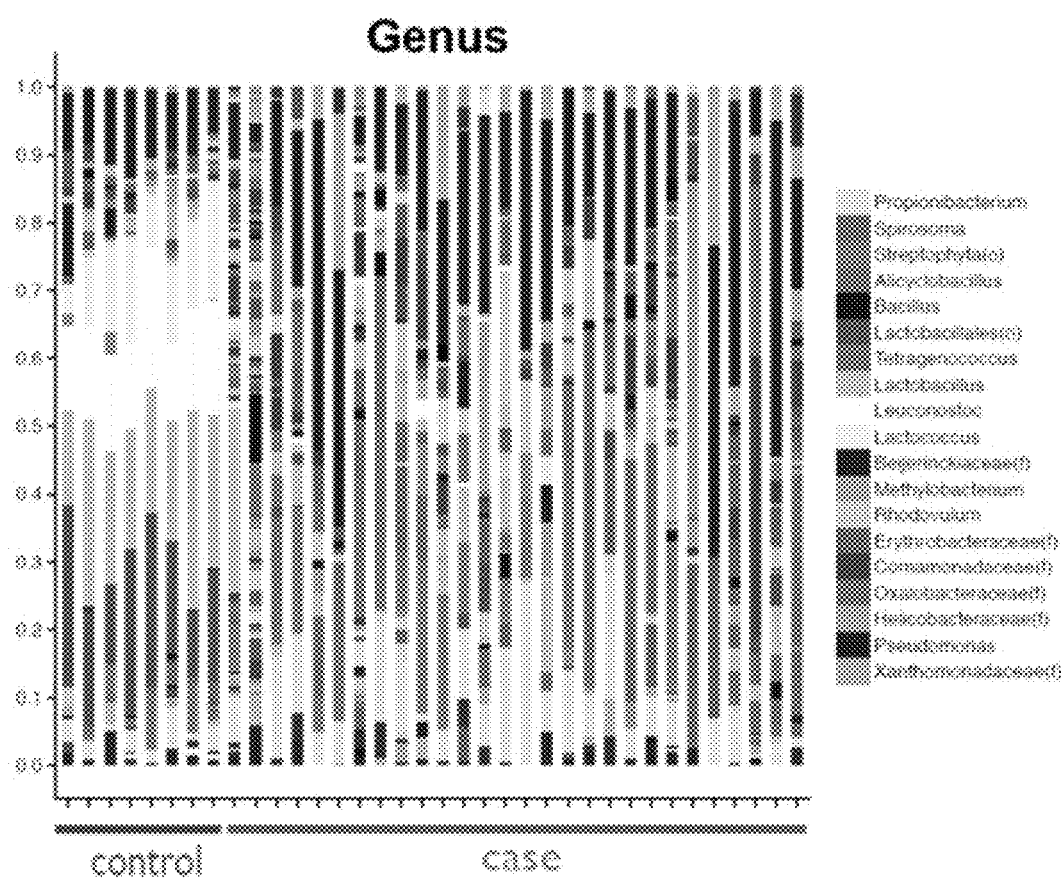
FIG. 16 shows the result of metagenomic analysis at a bacteria genus level to compare distribution of bacteria-derived EVs isolated from the urine of an atopic dermatitis patient and a normal person.

Ten minutes after the administration, images were obtained through two-photon microscopy, and as shown in FIG. 6, it was confirmed that EVs are found in the capillaries.

Example 3. Metagenomic Analysis of Bacteria-Derived EVs Using Urine and Serum of Atopic Dermatitis Patient 3-1. Isolation of EVs from Urine and Serum of Atopic Dermatitis Patient Based on the result that the absorbed bacteria-derived EVs are excreted in the urine and distributed in the blood according to Example 2, the bacteria-derived EVs present in the urine and the serum of an atopic dermatitis patient were isolated, and then DNA contained therein were extracted.

Among the patients visiting the Pediatric Allergy Respiratory Center of Soonchunhyang University, Seoul, atopic dermatitis patients up to the age of 17 years, which satisfy Hanifin and Rajka diagnostic criteria for atopic dermatitis, were targeted. Patients with other skin diseases or who had received topical, oral or injectable antibiotics within the last 14 days were excluded. As a normal control, infants not having any skin disorders including atopic dermatitis, allergic disease, a significant medical history and drug use were selected. Urine and serum samples were obtained from the patients in the atopic dermatitis patient group and the normal control, consenting to this research. Afterward, EVs were isolated from the urine and serum samples by the method of Example 1, boiled at a high temperature to extract DNA, and then quantification and qualification of the DNA were detected using a NanoDrop™ instrument before proceeding to the next step.

3-2. DNA Metagenomic Analysis Isolated from EVs Present in Urine and Serum

Metagenomic analysis was performed on DNA isolated from EVs present in the urine and serum samples of the atopic dermatitis patients by the method of Example 3-1.

First, PCR was performed on each clone for sequencing using 16s rDNA fusion primers and a FastStart High Fidelity PCR System (Roche, Basel, Switzerland) to amplify V1-V3 regions. The sequences of the 16s rDNA fusion primers are shown in Table 1.

TABLE 1

| Primer | | Sequence |
|---|---|---|
| 27F | Forward | 5'-GAGTTTGATCMTGGCTCAG-3' |
| 518R | Reverse | 5'-WTTACCGCGGCTGCTGG-3' |

PCR amplification was performed on emulsions prepared by mixing oil and amplicons to create "micro-reactors" containing an amplification mix and a single bead with TissueLyser II (Qiagen) and a GS-FLX plus emPCR Kit (454 Life Sciences). The emulsion was dispensed into a 96-well plate, and a 20-ng aliquot of each DNA sample was included in a 50-μl PCR reaction mix, followed by PCR proceeding according to the manufacturer's protocol (first step: 3 min at 94° C.; second step: 35 cycles of 15 sec at 94° C., 45 sec at 55° C., and 1 min at 72° C.; and final step: 8 min at 72° C.). Each DNA was amplified by emulsion PCR (emPCR), and the amplicons were purified using an AMpure Bead kit (Beckman Coulter, Brea, Calif., USA), and then quantified using a Picogreen method (Invitrogen, Carlsbad, Calif., USA). Subsequently, the amplicons were diluted and analyzed using a GS-FLX Titanium sequencer (Roche, Basel, Switzerland). After PCR amplification, each emulsion was chemically decomposed, and the beads with an amplified DNA library were washed through filtration. Positive beads were purified using biotinylated primer A (complementary to adaptor A), and attached to streptavidin-coated magnetic beads. Subsequently, the DNA library beads attached to the magnetic beads were separated from the magnetic beads by melting the double helix structure, and thus allowed single-stranded DNA to pass through. The sequencing primer was used again to create amplified single-stranded DNAs. Finally, the beads containing the amplified single-stranded DNA were counted using a particle counter (Beckman Coulter). Sequencing was performed using a Genome Sequencer FLX titanium (454 Life Sciences), and each sample was loaded into a 70 mm to 75 mm PicoTiter plate (454 Life Sciences).

For metagenomic analysis by bioinformatics, Phred quality scores (average Phred number >20) and read lengths (>300 bp) were checked to collect high-quality sequences. Operational taxonomic units (OUTs) were analyzed using UCLUST and USEARCH (Edgar, 2010), and phylogenetic classification was analyzed using QIIME (Lozupone, et al., 2006). Based on similarity, all of the 16s RNA sequences were classified at the following phylogenetic levels: species >97% similarity; genus >94% similarity; family >90% similarity; order >85% similarity; class >80% similarity; and phylum >75% similarity. Genus-level bacterial compositions were plotted as heat maps when a significant difference in compositions between the atopic dermatitis patient group and the normal control was detected to be two-fold or higher. Hierarchical clustering was performed when a significant difference in compositions was two-fold or higher or there was a 1% or higher average composition at the genus level between the atopic dermatitis patient group and the normal control.

3-3. Analysis of Relationship Between Bacteria-Derived EVs Present in Urine and Serum After DNA was isolated from bacteria-derived EVs present in the urine and serum of the atopic dermatitis patient according to the method of Example 3-1, the base sequence of 16S rDNA was analyzed through metagenomic analysis according to the method of Example 3-2 to compare distributions of bacteria-derived EVs present in the urine and serum.

FIGS. 7 to 11 show the results of metagenome analyses at phylum, class, order, family and genus levels, respectively, and EV distribution in the urine sample (boiled urine) of each patient is indicated by a red underline, and EV distribution in the serum sample (serum) thereof is indicated by a blue underline. As a result, it can be seen that the distribution of the bacteria-derived EVs present in the urine and the distribution of the bacteria-derived EVs present in the serum of the atopic dermatitis patient exactly match.

Example 4. Analysis of Difference in Distribution of Bacteria-Derived EVs in Urine of Atopic Dermatitis Patient and Normal Person A difference in distribution of the bacteria-derived EVs in the urine of the atopic dermatitis patient and the normal person was evaluated according to the methods of Examples 3-1 and 3-2.

FIGS. 12 to 16 show the results of the metagenome analyses at phylum, class, order, family and genus levels, respectively, and EV distribution in the urine sample of the normal person (control) is indicated by a blue underline, and EV distribution in the urine sample of the atopic dermatitis patient (case) is indicated by a red underline.

Figure 17:
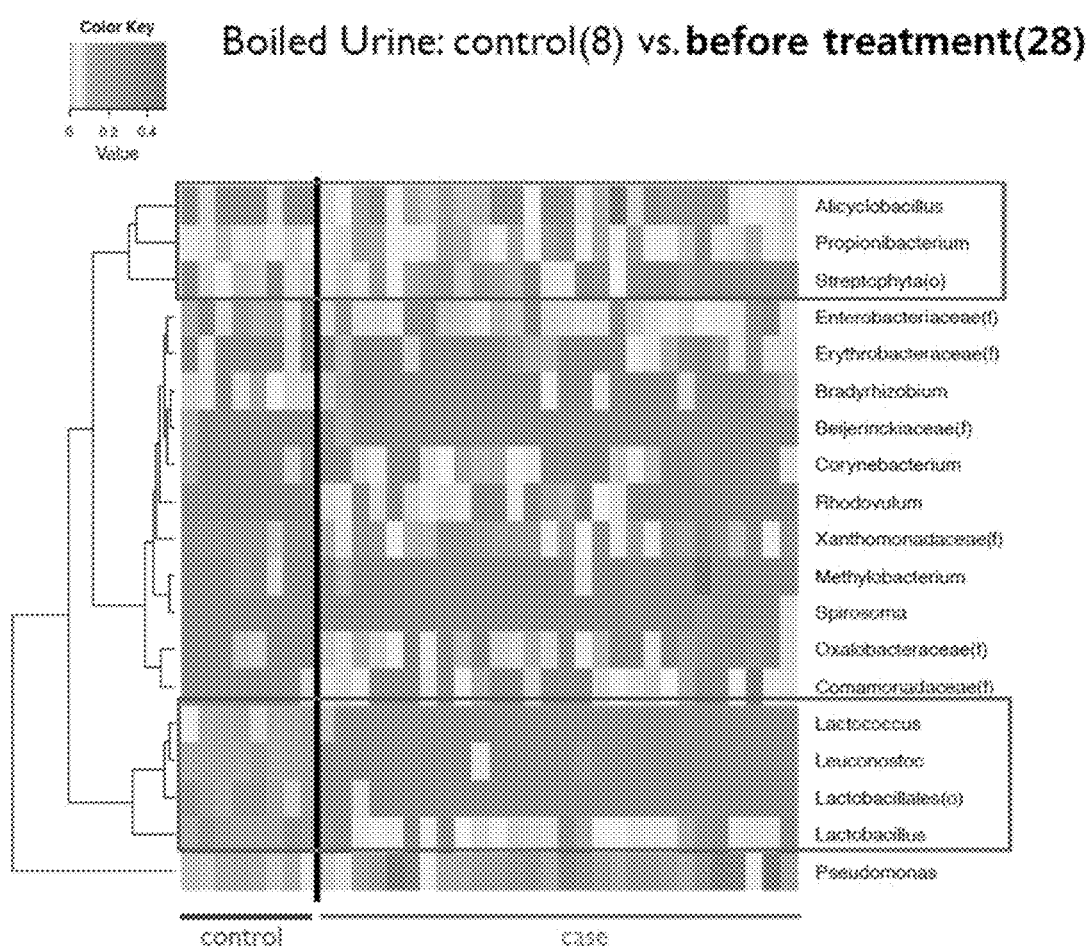
FIG. 17 is a heat map showing the result of metagenomic analysis of bacteria-derived EVs isolated from the urine of an atopic dermatitis patient and a normal person.

As a result, it was confirmed that there are significant differences in the distribution of bacteria-derived EVs in the urine of the atopic dermatitis patient and the normal person at all of phylum, class, order, family and genus levels. More specifically, as shown in FIG. 17 and Table 1 below, among bacteria-derived EVs present at 1% or more in the urine, *Alicyclobacillus*-derived EVs (normal person vs. atopic dermatitis patient: 0.31% vs. 8.49%), *Methylobacterium*-derived EVs (normal person vs. atopic dermatitis patient: 0.22% vs. 2.02%), Streptophyta-derived EVs (normal person vs. atopic dermatitis patient: 2.87% vs. 7.89%), *Propionibacterium*-derived EVs (normal person vs. atopic dermatitis patient: 2.78% vs. 7.6%), and *Pseudomonas*-derived EVs (normal person vs. atopic dermatitis patient: 9.56% vs. 21.91%) are significantly increased in the urine of the atopic dermatitis patients (case) compared to the normal person (control). However, among the bacteria-derived EVs present in the urine at 1% or more, it was confirmed that *Lactobacillus*-derived EVs (normal person vs. atopic dermatitis patient: 20.92% vs. 4.61%), *Leuconostoc*-derived EVs (normal person vs. atopic dermatitis patient: 14.60% vs. 0.12%), Lactobacillales-derived EVs (normal person vs. atopic dermatitis patient: 18.19% vs. 0.05%), and *Lactococcus*-derived EVs (normal person vs. atopic dermatitis patient: 11.57% vs. 0.03%) are significantly decreased in the urine of the atopic dermatitis patients compared to the normal person.

TABLE 2

| Taxon | mean of control | mean of case | fold change (>2) |
|---|---|---|---|
| *Spirosoma* | 0.00% | 1.01% | |
| *Rhodovulum* | 0.00% | 2.11% | |
| Comamonadaceae(f) | 0.13% | 3.88% | 30.19119825 |
| *Alicyclobacillus* | 0.31% | 8.49% | 27.51403969 |
| Xanthomonadaceae(f) | 0.22% | 2.90% | 13.06785494 |
| Oxalobacteraceae(f) | 0.21% | 2.43% | 11.60697873 |
| *Methylbacterium* | 0.22% | 2.02% | 9.012406882 |
| *Corynebacterium* | 0.22% | 1.04% | 4.756459494 |
| Erythrobacteraceae(f) | 0.41% | 1.22% | 2.968795879 |
| Streptophyta(o) | 2.87% | 7.89% | 2.753642811 |
| *Propionibacterium* | 2.78% | 7.60% | 2.735314802 |
| Enterobacteriaceae(f) | 0.70% | 1.63% | 2.308796704 |
| *Pseudomonas* | 9.56% | 21.91% | 2.290976998 |
| *Lactobacillus* | 20.92% | 4.61% | −4.532536438 |
| *Bradyrhizobium* | 1.66% | 0.34% | −4.905485845 |
| Beijerinckiaceae(f) | 1.33% | 0.02% | −83.67457993 |
| *Leuconostoc* | 14.60% | 0.12% | −125.9090135 |
| Lactobacillales(o) | 18.19% | 0.05% | −331.1640723 |
| *Lactococcus* | 11.57% | 0.03% | −423.8955206 |

Example 5. Isolation and Analysis of Characteristics of EVs in Culture of Lactic Acid Bacteria From the result of Example 4, since it was confirmed that the Lactobacillales and *Lactobacillus*-derived EVs are significantly decreased in the urine of the atopic dermatitis patients compared to the normal persons, the effects of immune responses and inflammation responses on the *Lactobacillus*-derived EVs were investigated.

To this end, lactic acid bacteria such as *Lactobacillus plantarum* isolated from kimchi were cultured, and then a culture of the lactic acid bacteria was centrifuged at 10,000×g for 20 minutes, followed by collecting only a supernatant and filtering it with a 0.22-mm filter. After EVs in the separated filtrate, having a size of 100 kDa or larger, were concentrated at a certain amount, and ultracentrifuged at 150,000×g and 4° C. for 3 hours, the EV cluster remaining after the supernatant was discarded was diluted with normal saline (PBS), and then its concentration was measured using a BCA protein assay (Pierce, USA). Afterward, to confirm that physical properties of EVs isolated from the lactic acid bacteria are the same, dynamic light scattering and electron microscopy were performed.

Figure 18:
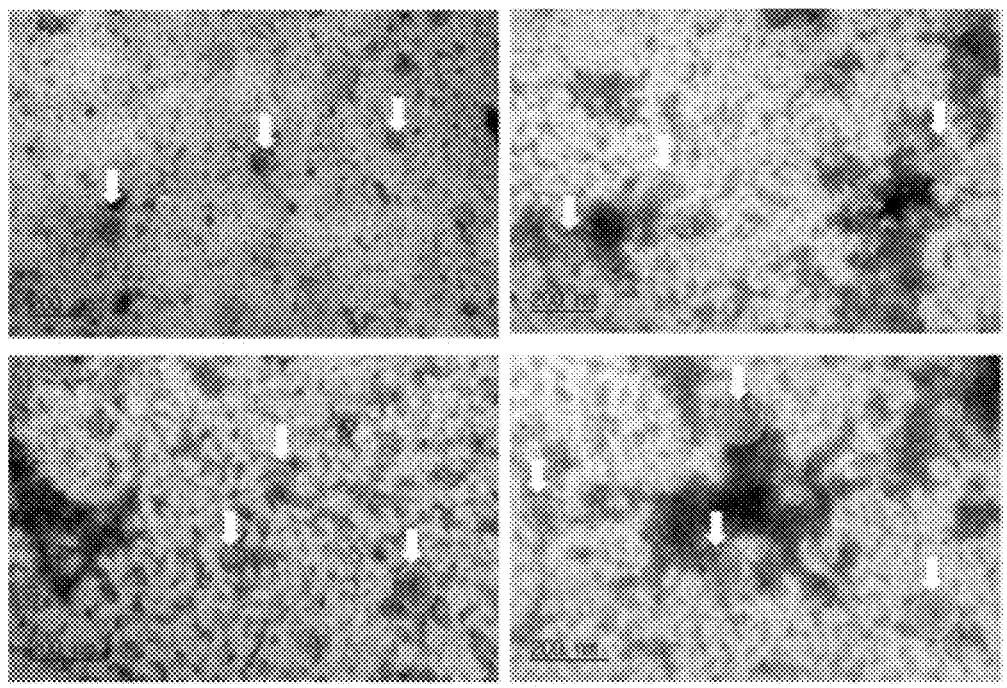
FIG. 18 shows images of EVs isolated from a culture of *Lactobacillus plantarum*, obtained using an electron microscope.
Figure 19:
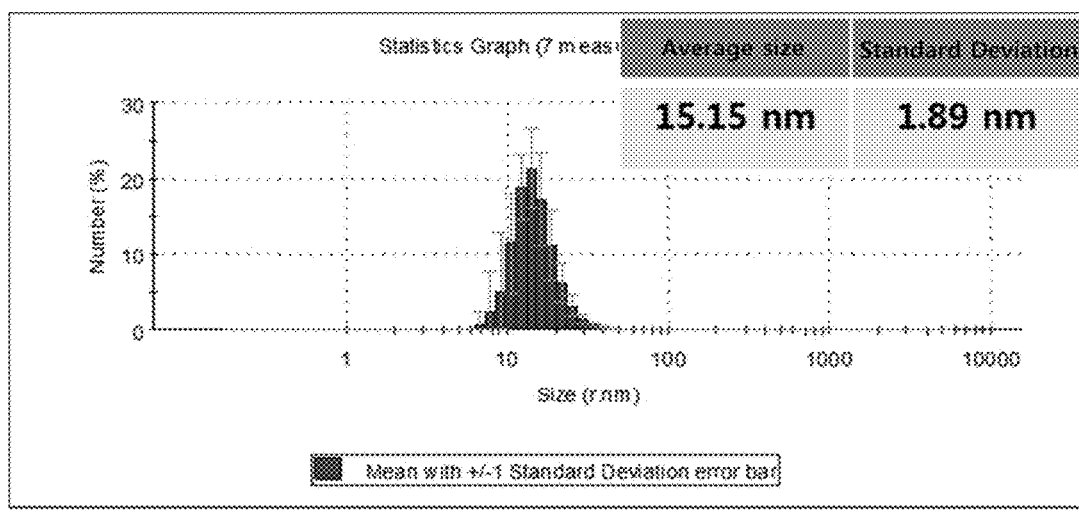
FIG. 19 shows the sizes of EVs isolated from a culture of *Lactobacillus plantarum* by dynamic light scattering.

Through the electron microscopy, as shown in FIG. 18, it was observed that the lactic acid bacteria-derived EVs have spherical shapes, and as shown in FIG. 19, it was confirmed that they have an average diameter of approximately 15 nm through the dynamic light scattering.

Figure 20:
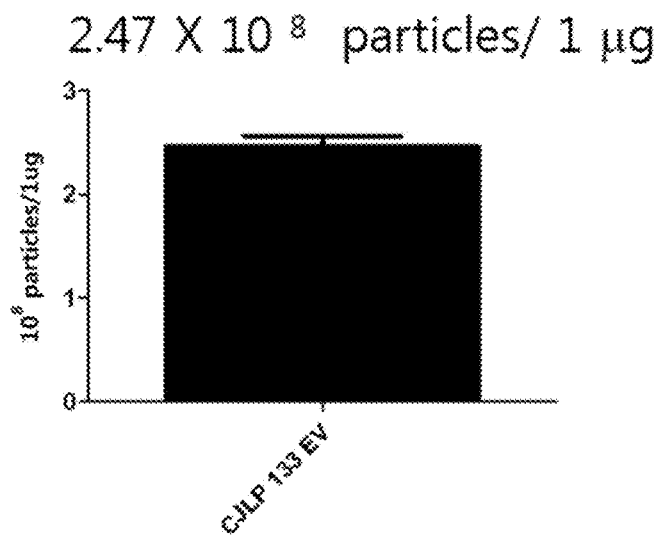
FIG. 20 shows the number of EVs isolated from a culture of *Lactobacillus plantarum* by a nanotrafficking assay (NTA).

Afterward, to identify an amount of the isolated EVs, a nanoparticle tracking analysis (NanoSight: LM10HS) was performed. After 2 ml of an EV sample adjusted to a concentration of 500 ng/ml was prepared, 0.3 to 0.4 ml of the sample was placed in a chamber of the LM-10HS instrument, and focused using a camera so that particles are clearly visible. After the camera was raised to the maximum level while being focused, the sample was captured by the stepwise lowering of the level to confirm whether there was no drift of the sample. After confirming the concentration, focus and drift of the sample, a capture duration was set to 30 seconds and thus data was obtained. As a result, as shown in FIG. 20, it was confirmed that $2.47 \times 10^8$ EVs are present based on 1 μg of protein.

Figure 21:
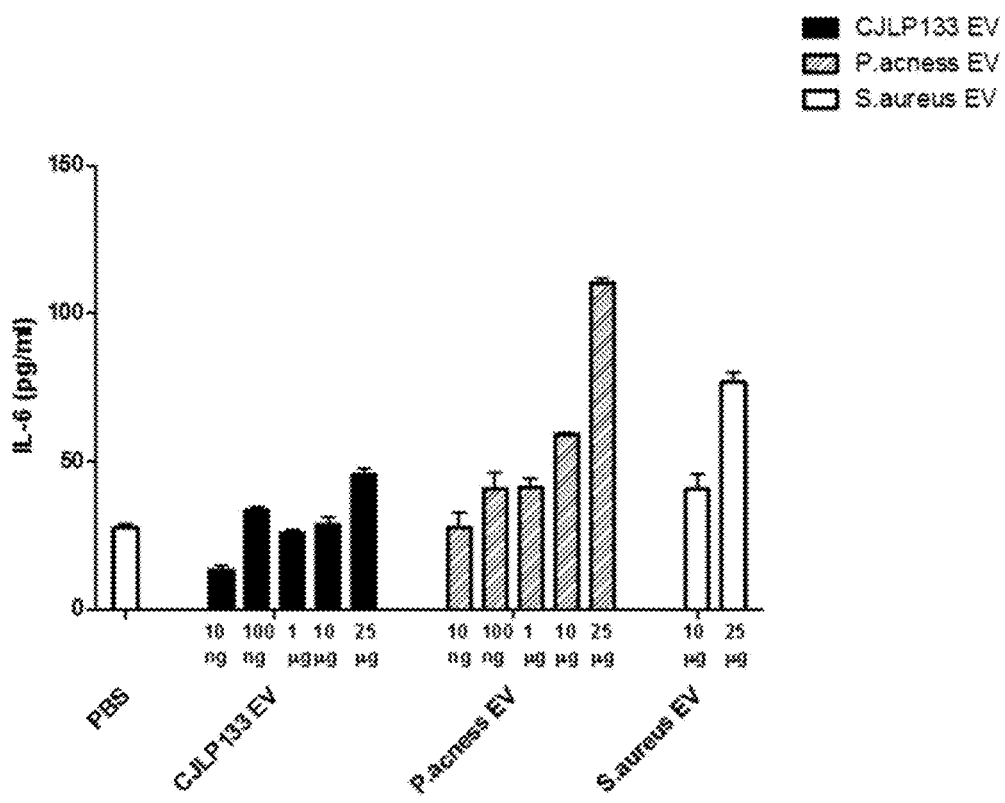
FIG. 21 shows IL-6 secretion levels measured by ELISA, after *S. aureus*-derived EVs (*S. aureus* EV), *Propionibacterium* acne-derived EVs (*P. acnes* EV), and lactic acid bacteria-derived EVs (CJLP133 EV) are administered to dermal epithelial cells.

Example 6. Identification of Immune Modulating Effect of Lactic Acid Bacteria-Derived EVs on Immune Responses Triggered by *S. aureus* EV Stimulation in Dermal Epithelial Cells To see the effect of lactic acid bacteria-derived EVs in inflammatory responses, $2 \times 10^5$ cells of a dermal epithelial cell line (HaCaT) were treated with *S. aureus*-derived EVs (*S. aureus* EV) and *Propionibacterium* acne-derived EVs (*P. acnes* EV), known as the main causative agents of inflammatory diseases, and lactic acid bacteria-derived EVs (CJLP133 EV) isolated by the method of Example 5 at concentrations of 10 ng to 25 μg/ml, respectively, cultured for 12 hours, and a secretion level of cytokine IL-6 causing a Th17 immune response in a supernatant was detected by ELISA. As a result, as shown in FIG. 21, compared to *S. aureus* and *Propionibacterium* acne-derived vesicles, when treated with the lactic acid bacteria-derived EVs, it was identified that the secretion level of IL-6 was considerably lower.

Figure 22:
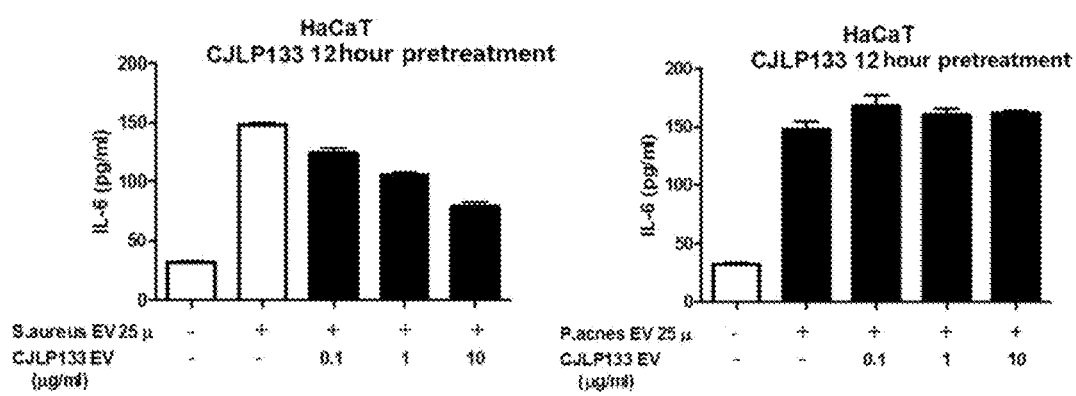
FIG. 22 shows IL-6 secretion levels measured by ELISA, after lactic acid bacteria-derived EVs (CJLP133 EV) are administered 12 hours before *S. aureus*-derived EVs (*S. aureus* EV), or *Propionibacterium* acne-derived EVs (*P. acnes* EV) are administered to dermal epithelial cells.

In addition, dermal epithelial cells treated with the lactic acid bacteria-derived EVs at various concentrations (0.1, 1, and 10 μg/ml) 12 hours before were treated with 25 μg/ml of *S. aureus* or *Propionibacterium* acne-derived vesicles and then cultured for 12 hours, followed by identifying a secretion level of inflammatory cytokine IL-6 in a supernatant by ELISA. As a result, as shown in FIG. 22, when the lactic acid bacteria-derived EVs (*S. aureus* EV) were pre-treated, IL-6 secretion caused by the *S. aureus*-derived vesicles was concentration-dependently decreased, but there was no effect of the lactic acid bacteria-derived EVs on IL-6 secretion caused by the *Propionibacterium* acne-derived vesicles (*P. acnes* EV).

Such a result shows that the lactic acid bacteria-derived EVs inhibited the Th1-mediated immune response and inflammation responses by the *S. aureus*-derived EVs, and specifically acts on an abnormality of the immune function caused by the *S. aureus*-derived EVs.

Figure 23:
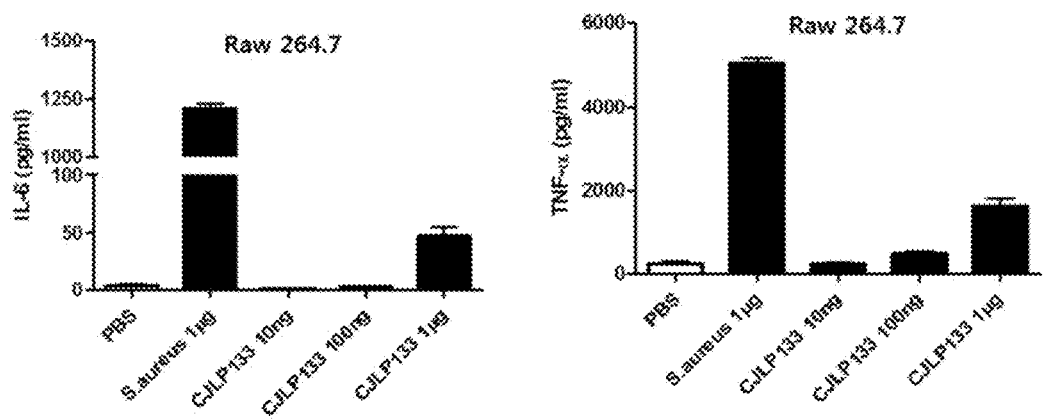
FIG. 23 shows IL-6 and TNF-α secretion levels measured by ELISA, after *S. aureus*-derived EVs (*S. aureus* EV), or lactic acid bacteria-derived EVs (CJLP133 EV) are administered to peritoneal macrophages.

Example 7. Identification of Antiinflammatory Effect of Lactic Acid Bacteria-Derived EVs on Inflammatory Responses by *S. aureus*-Derived EV Stimulation in Inflammatory Cells The effect of the lactic acid bacteria-derived EVs on the inflammation responses triggered by the *S. aureus*-derived EVs in inflammatory cells was examined. First, inflammatory cells, that is, a mouse peritoneal macrophage line (Raw 264.7) was treated with 1 μg of *S. aureus*-derived EVs (*S. aureus*), or 10 ng, 100 ng or 1 μg of lactic acid bacteria-derived EVs (CJLP133) for 12 hours, and thus amounts of inflammatory cytokines IL-6 and TNF-α secreted from peritoneal macrophages were detected and compared. As a result, as shown in FIG. 23, when treated with the lactic acid bacteria-derived EVs, compared to treatment with the *S. aureus*-derived vesicles, IL-6 and TNF-α secretion was significantly decreased regardless of concentration. This means that, compared to the *S. aureus*-derived vesicles, when the lactic acid bacteria-derived EVs were absorbed in the mouse, it is much safer.

Figure 24:
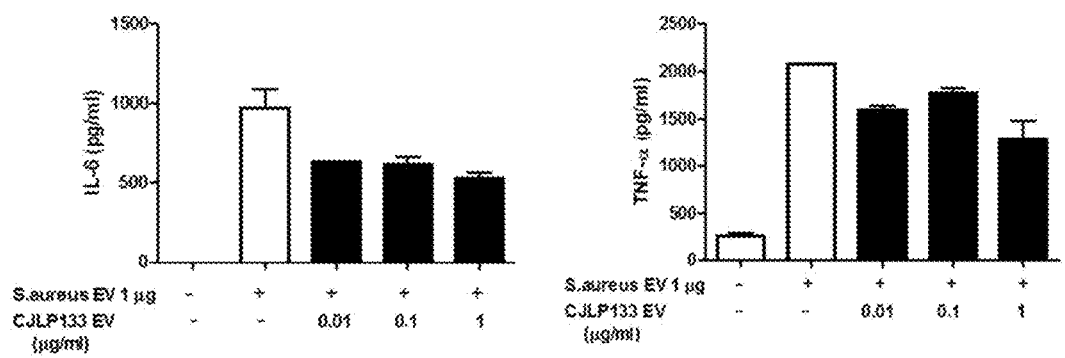
FIG. 24 shows IL-6 and TNF-α secretion levels measured by ELISA, after lactic acid bacteria-derived EVs (CJLP133 EV) are administered 12 hours before *S. aureus*-derived EVs (*S. aureus* EV) are administered to peritoneal macrophages.

Based on the result, the mouse peritoneal macrophage line was treated with the lactic acid bacteria-derived EVs at various concentrations (0.01, 0.1 and 1 μg/ml), 12 hours later, the *S. aureus*-derived EVs were treated at a concentration of 1 μg/ml, and then another 12 hours later, amounts of the inflammatory cytokines IL-6 and TNF-α were detected by ELISA. As a result, as shown in FIG. 24, it was confirmed that, when the lactic acid bacteria-derived EVs were pre-treated, the IL-6 and TNF-α secretion caused by the *S. aureus*-derived EVs is inhibited. This means that the lactic acid bacteria-derived EVs can effectively inhibit inflammation responses of inflammatory cells triggered by the *S. aureus*-derived EVs.

Figure 25:
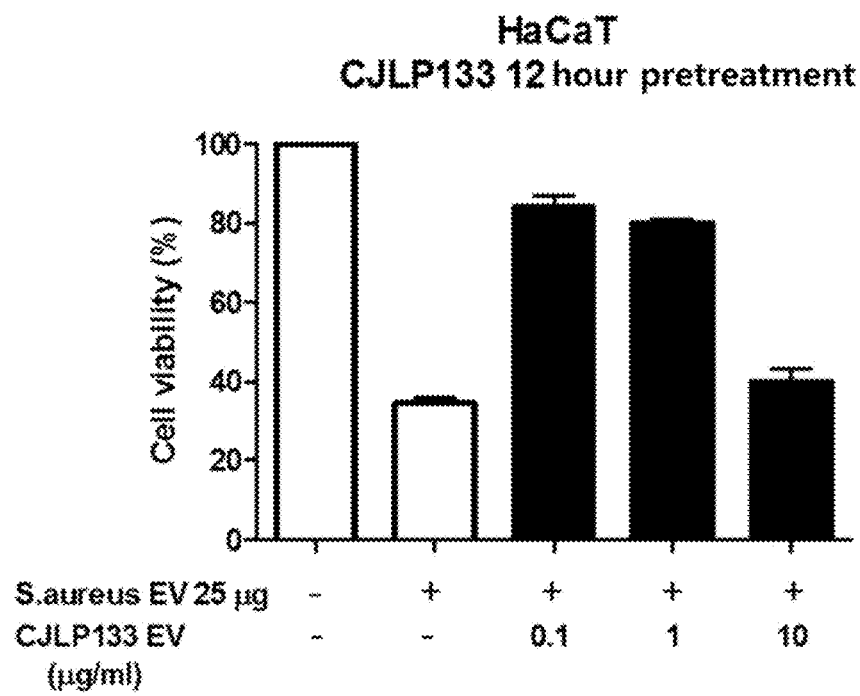
FIG. 25 shows a degree of apoptosis evaluated by MTT assays, after lactic acid bacteria-derived EVs (CJLP133 EV) are administered 12 hours before *S. aureus*-derived EVs (*S. aureus* EV) are administered to dermal epithelial cells.

Example 8. Identification of Inhibitory Effect on Apoptosis of Lactic Acid Bacteria-Derived EVs in Apoptosis of Dermal Epithelial Cells by *S. aureus*-Derived EV Stimulation To evaluate inhibitory effect on the apoptosis of lactic acid bacteria-derived EVs in the apoptosis of dermal epithelial cells caused by *S. aureus*-derived EVs, dermal epithelial cells were pre-treated with lactic acid bacteria-derived EVs at the same concentration under the same conditions used in Example 6, followed by treating *S. aureus*-derived vesicles (*S. aureus* EV) at a concentration of 25 μg for 24 hours, and performing MTT assay (Sigma, USA). As a result, as shown in FIG. 25, it was confirmed that the apoptosis of the dermal epithelial cells caused by the *S. aureus*-derived vesicles is effectively inhibited by the treatment of the lactic acid bacteria-derived EVs at a concentration of 0.1 μg/ml or 1 μg/ml.

Example 9. Identification of Antiinflammatory Effect of Lactic Acid Bacteria-Derived EVs on Inflammation Caused by *P. aeruginosa*-Derived EVs

*P. aeruginosa* is the antibiotic-resistant main pathogenic bacteria belonging to the genus *Pseudomonas*, and also known as the main causative bacteria of sepsis. Recently, *P. aeruginosa*-derived EVs have been known as the main causative agent of a chronic lung disease such as asthma, chronic obstructive pulmonary disease (COPD) or lung cancer, due to repeated exposure through the airway. With this background, an antiinflammatory effect of lactic acid bacteria-derived EVs on inflammation responses caused by the *P. aeruginosa*-derived vesicles was evaluated.

Figure 26:
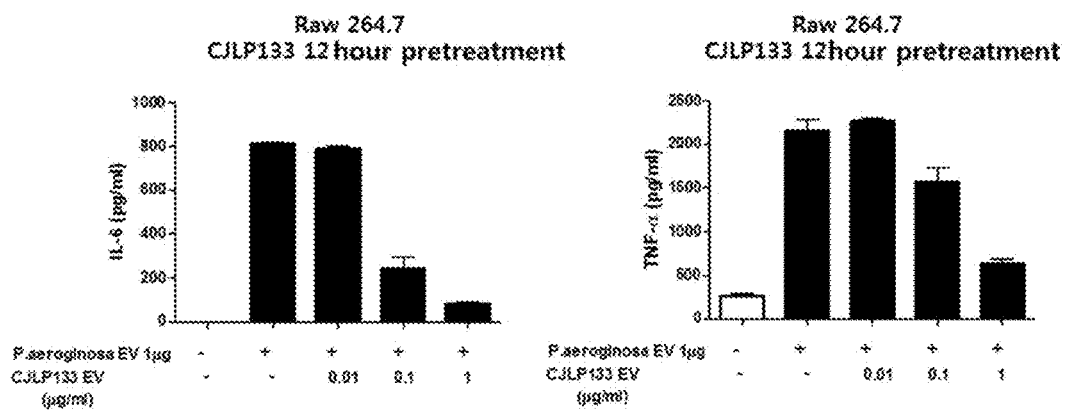
FIG. 26 shows IL-6 and TNF-α secretion levels measured by ELISA, after lactic acid bacteria-derived EVs (CJLP133 EV are administered 12 hours before *Pseudomonas aeruginosa*-derived EVs (*P. aeruginosa* EV) are administered to peritoneal macrophages.

To this end, inflammatory cells, a peritoneal macrophage line (Raw 264.7), were treated with lactic acid bacteria-derived EVs (CJLP133 EV) at various concentrations (0.01, 0.1, and 1 μg/ml), 12 hours later, *P. aeruginosa*-derived EVs (*P. aeruginosa* EV) were treated at a concentration of 1 μg/ml, and then concentrations of inflammatory cytokines IL-6 and TNF-α were detected by ELISA. As a result, as shown in FIG. 26, it was confirmed that the secretion of IL-6 and TNF-α by *P. aeruginosa*-derived vesicle stimulation is almost perfectly inhibited in proportion to a concentration of the lactic acid bacteria-derived EVs treated.

Figure 27:
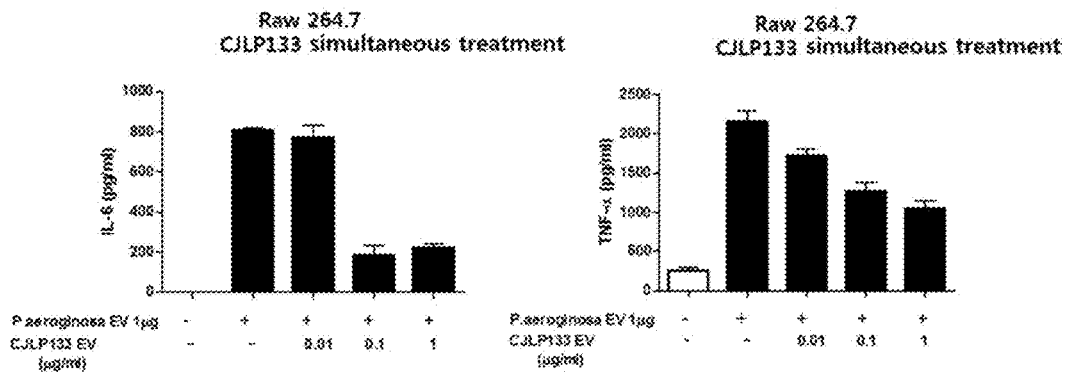
FIG. 27 shows IL-6 and TNF-α secretion levels measured by ELISA, after *Pseudomonas aeruginosa*-derived EVs (*P. aeruginosa* EV) are administered to peritoneal macrophages together with lactic acid bacteria-derived EVs (CJLP133 EV).

In addition, according to evaluation of simultaneous treatment of a peritoneal macrophage line with the *P. aeruginosa*-derived EVs and the lactic acid bacteria-derived EVs and secretion levels of the inflammatory cytokines, as shown in FIG. 27, it was confirmed that the IL-6 and TNF-α secretion caused by *P. aeruginosa*-derived EV stimulation is significantly inhibited by treatment of the lactic acid bacteria-derived vesicles. The above results show that inflammation caused by *P. aeruginosa*-derived vesicles known as a causative factor of the chronic lung disease and sepsis is effectively inhibited by the lactic acid bacteria-derived vesicles.

Example 10. Identification of Inhibitory Effect on Atopic Dermatitis Due to *S. aureus*-Derived EVs by Dermal Administration of Lactic Acid Bacteria-Derived EVs Since effects of inhibiting immune modulation, antiinflammation, and dermal cell apoptosis, caused by the *S. aureus*-derived EVs, by the lactic acid bacteria-derived EVs were identified according to Examples 6 to 8, a practical atopic dermatitis-treating effect by dermal administration of lactic acid bacteria-derived EVs was evaluated.

Figure 28:
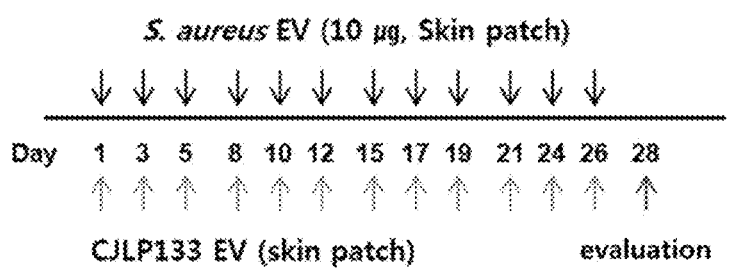
FIG. 28 shows the protocol for evaluating therapeutic effects caused by dermal administration of lactic acid bacteria-derived EVs (CJLP133 EV) in atopic dermatitis mouse models caused by *S. aureus*-derived EVs (*S. aureus* EV).

To this end, according to the protocol illustrated in FIG. 28, SKH-1 hairless mice were repeatedly coated with 10 μg of the *S. aureus*-derived EVs (*S. aureus* EV) three times a week for 4 weeks to produce an atopic dermatitis model, 12 hours before the *S. aureus*-derived EVs were coated, a therapeutic effect on the development of atopic dermatitis was observed by coating the skin with the lactic acid bacteria-derived EVs (CJLP133 EV). Here, as a positive control, an immunosuppressant used as a medication for atopic dermatitis, dexamethasone, was intraperitoneally injected at a concentration of 300 μg, and the experiment was carried out under the same conditions.

Figure 29:
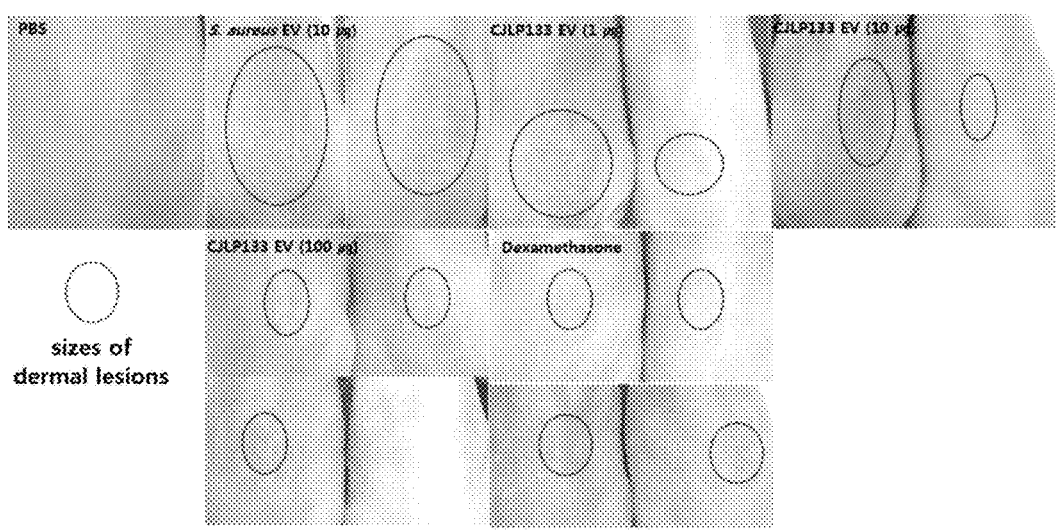
FIG. 29 shows images of skin, taken to evaluate therapeutic effects after lactic acid bacteria-derived EVs (CJLP133 EV) are percutaneously administered in atopic dermatitis mouse models caused by *S. aureus*-derived EVs (*S. aureus* EV).

As a result, as shown in FIG. 29, when an atopic dermatitis mouse model induced by *S. aureus*-derived EVs was coated with lactic acid bacteria-derived EVs, compared to an uncoated mouse model, sizes of dermal lesions were decreased, and when 100 μg of the lactic acid bacteria-derived vesicles were administered, it was confirmed that dermal lesions were inhibited similar to the case of intraperitoneally administration of the immunosuppressant dexamethasone.

Figure 30:
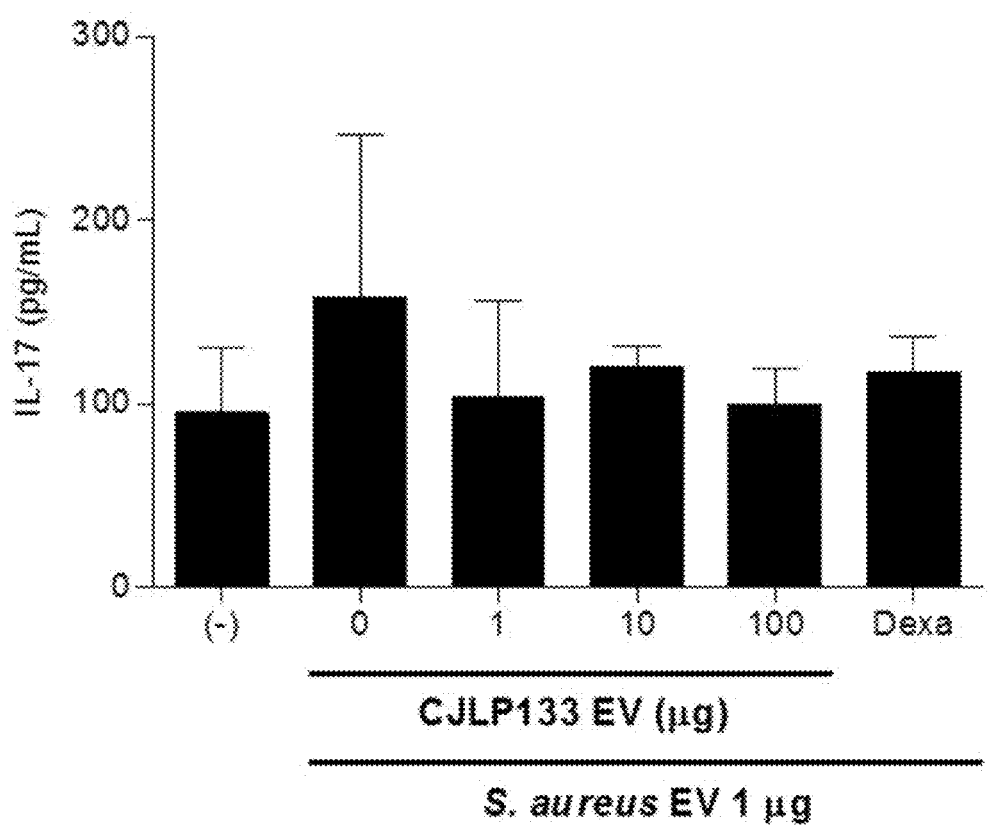
FIG. 30 shows IL-17 concentrations in dermal tissue after lactic acid bacteria-derived EVs (CJLP133 EV) are percutaneously administered to atopic dermatitis mouse models caused by *S. aureus*-derived EVs (*S. aureus* EV).

In addition, as a result of measuring a representative immune marker IL-17 causing Th17 inflammation in dermal tissue, as shown in FIG. 30, when lactic acid bacteria-derived EVs were applied to the skin, compared to the lactic acid bacteria-derived EVs were not applied, a low concentration of IL-17 was detected, which was similar to that of the positive control (dexa). The above result shows that, when the lactic acid bacteria-derived EVs were percutaneously administered, dermal inflammatory diseases such as atopic dermatitis can be effectively inhibited.

Example 11. Identification of Therapeutic Effect of Oral Administration of Lactic Acid Bacteria-Derived EVs on Dermal Inflammation Caused by *S. aureus*-Derived EVs To evaluate the effect of treating atopic dermatitis by the oral administration of lactic acid bacteria-derived EVs, according to the protocol illustrated in FIG. 31, 10 μg of *S. aureus*-derived vesicles (*S. aureus* EV) were repeatedly applied to SKH-1 hairless mice three times a week for four weeks to produce an atopic dermatitis model, and 12 hours before the *S. aureus*-derived vesicles were applied, the therapeutic effect on the development of atopic dermatitis was observed by orally administering lactic acid bacteria-derived EVs (CJLP133 EV).

Figure 32:
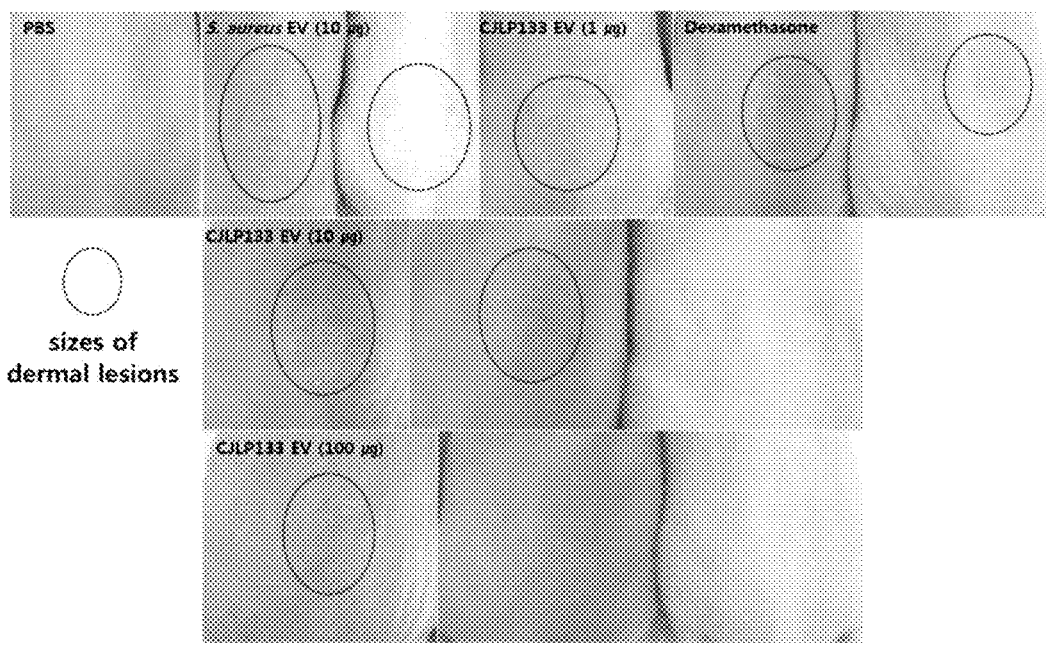
FIG. 32 shows images of skin, taken to evaluate therapeutic effects after lactic acid bacteria-derived EVs (CJLP133 EV) are orally administered in atopic dermatitis mouse models caused by *S. aureus*-derived EVs (*S. aureus* EV).

As a result, as shown in FIG. 32, when the lactic acid bacteria-derived EVs are orally administered, compared to when the lactic acid bacteria-derived EVs were not administered, the sizes of dermal lesions were decreased, and in some mice to which the lactic acid bacteria-derived vesicles were administered at 10 μg or 100 μg, no dermal lesions were observed.

Figure 33:
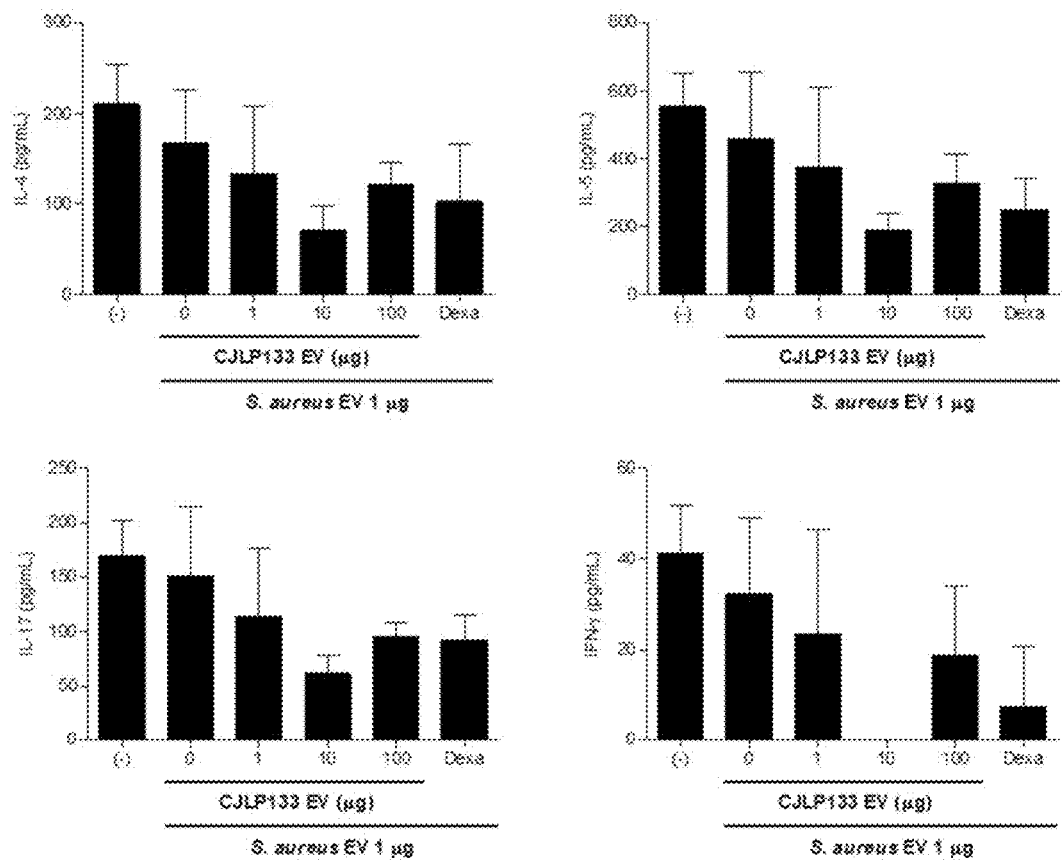
FIG. 33 shows concentrations of IL-4, IL-6, IL-17, and IFN-γ, which are immune response markers, in dermal tissue after lactic acid bacteria-derived EVs (CJLP133 EV) are orally administered to atopic dermatitis mouse models caused by *S. aureus*-derived EVs (*S. aureus* EV).

In addition, to evaluate immune and inflammatory markers in dermal tissue, as a result of measuring IL-4, IL-5, IL-17, and IFN-γ concentrations in the dermal tissue, as shown in FIG. 33, when lactic acid bacteria-derived EVs were orally administered, it was confirmed that secretion of the cytokines were significantly inhibited. The above result shows that, when the lactic acid bacteria-derived EVs were orally administered, a dermal inflammatory disease such as atopic dermatitis was effectively inhibited.

Figure 34:
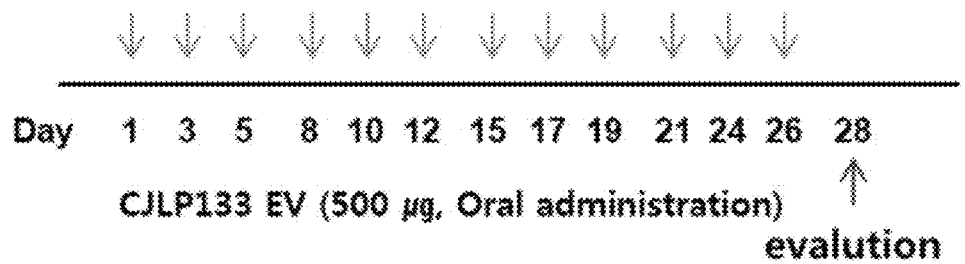
FIG. 34 shows the protocol for evaluating toxicity by high-dose oral administration of lactic acid bacteria-derived EVs (CJLP133 EV).

Example 12. Evaluation of Safety by Multiple Oral Administration of High Dose of Lactic Acid Bacteria-Derived EVs To evaluate toxicity generated by high-dose repeated administration of lactic acid bacteria-derived EVs, 500 μg of lactic acid bacteria-derived EVs (CJLP133) were orally administered three times a week for four weeks (total 12 times) by the method illustrated in FIG. 34. Afterward, in a control in which the vesicles were not administered and a group to which lactic acid bacteria-derived vesicles were orally administered, the body weight, feed intake, and body temperature of each mouse were detected.

Figure 35:
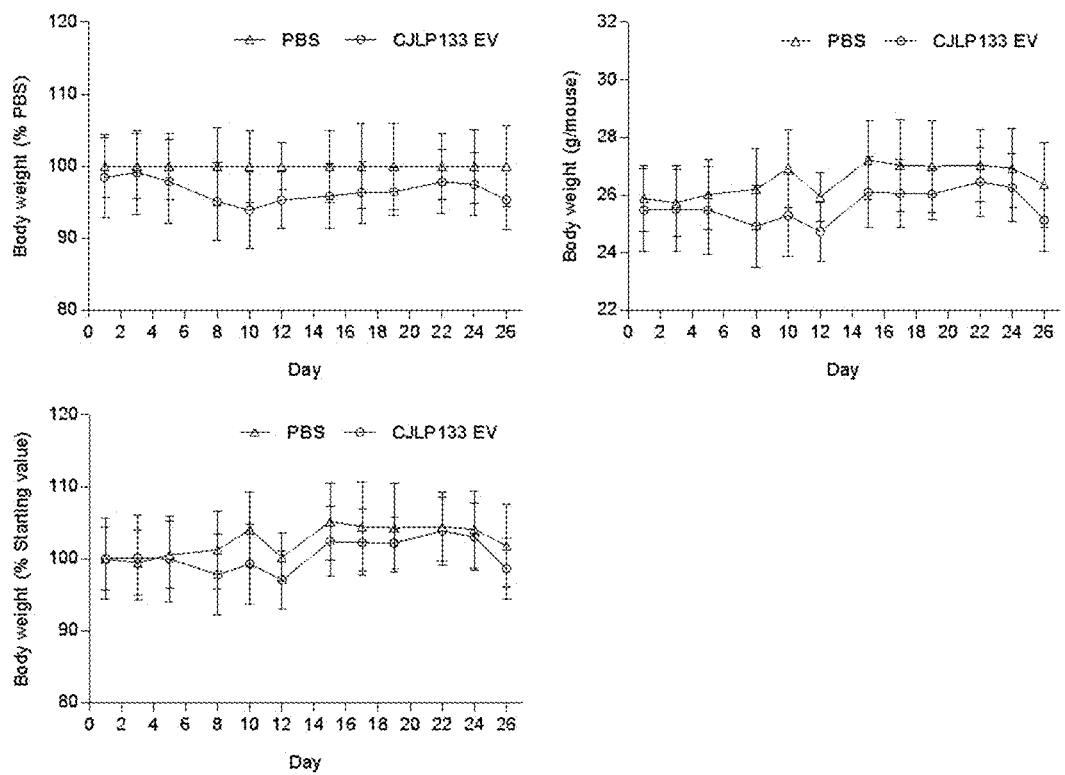
FIG. 35 shows changes in body weights after high doses of lactic acid bacteria-derived EVs (CJLP133 EV) are orally administered multiple times.
Figure 36:
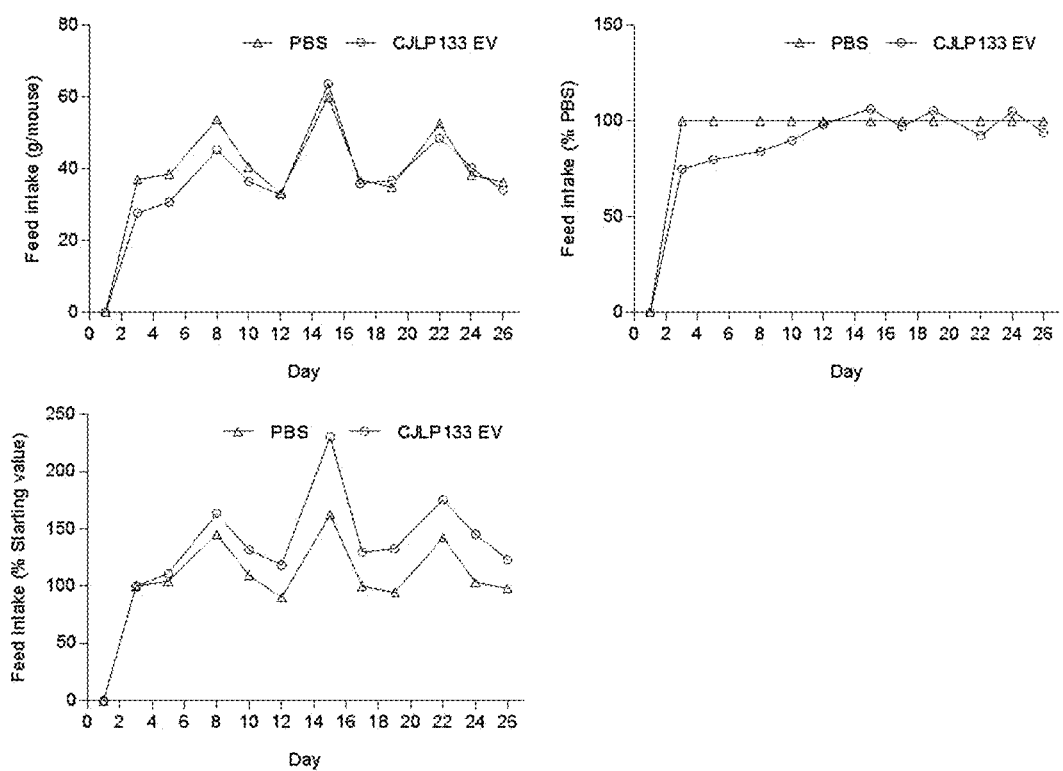
FIG. 36 shows the feed intake of mice after high doses of lactic acid bacteria-derived EVs (CJLP133 EV) are orally administered multiple times.
Figure 37:
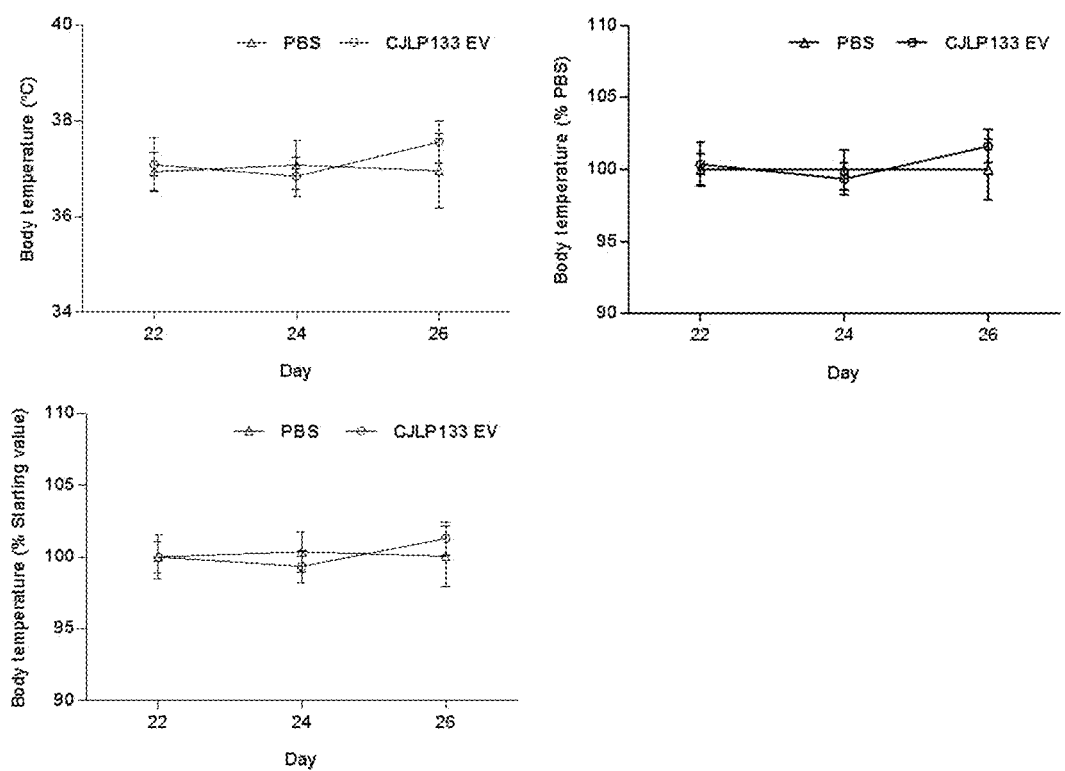
FIG. 37 shows the changes in body temperatures after high doses of lactic acid bacteria-derived EVs (CJLP133 EV) are orally administered multiple times.

As a result, as shown in FIGS. 35 to 37, it was confirmed that there were no significant differences between all of the three indexes in the control and the group to which the lactic acid bacteria-derived vesicles were administered.

Figure 38:
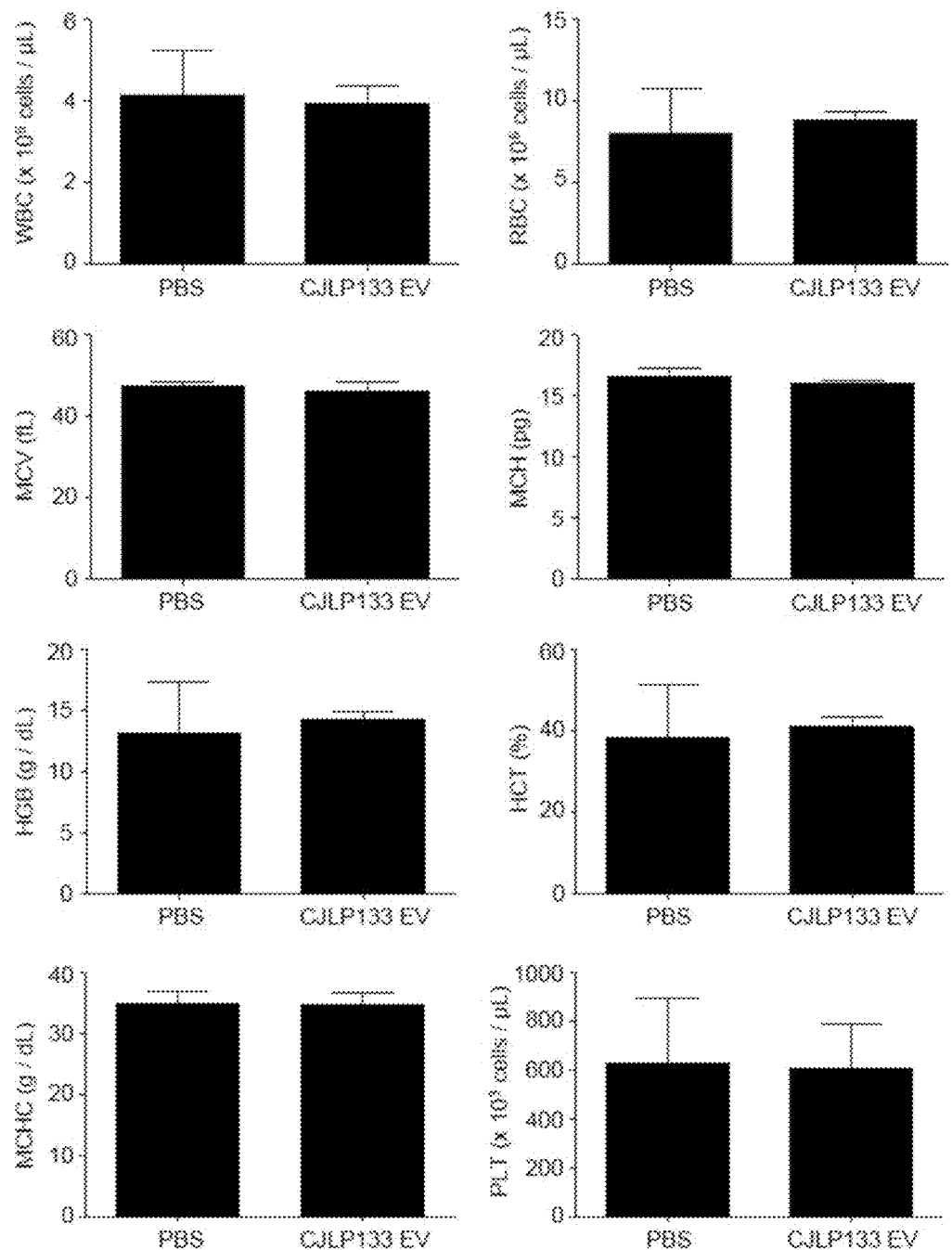
FIG. 38 shows the changes in blood cells in the blood after high doses of lactic acid bacteria-derived EVs (CJLP133 EV) are orally administered multiple times (WBC: the number of white blood cells, RBC: the number of red blood cells, HGB: the concentration of hemoglobins, HCT: hematocrit, MCV: mean corpuscular volume (mean volume of red blood cells), MCH: mean corpuscular hemoglobin (mean number of hemoglobins), MCHC: mean corpuscular hemoglobin concentration (mean concentration of hemoglobins), and PLT: the number of platelets).

In addition, 4 weeks after the oral administration, the blood was extracted to analyze blood cell ingredients, resulting in that there was no significant difference in 8 types of indexes shown in FIG. 38 (WBC: the number of white blood cells, RBC: the number of red blood cells, HGB: the concentration of hemoglobin, HCT: hematocrit, MCV: mean corpuscular volume, MCH: mean corpuscular hemoglobin, MCHC: mean corpuscular hemoglobin concentration, and PLT: the number of platelets) between the control and the group to which the lactic acid bacteria-derived EVs were administered. The above result shows that the lactic acid bacteria-derived EVs can safely exhibit a therapeutic effect when orally administered at a high dose.

It would be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

<210> 1
<211> 19
<212> DNA
<213> Artificial Sequence
<220>
<223> 16s rDNA fusion primer_27F
<400> 1
gagtttgatc mtggctcag 19
<210> 2
<211> 17
<212> DNA
<213> Artificial Sequence
<220>
<223> 16s rDNA fusion primer_518R
<400> 2
wttaccgcgg ctgctgg 17

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: 16s rDNA fusion primer_27F

<400> SEQUENCE: 1
gagtttgatc mtggctcag                                                19

<210> SEQ ID NO 2
<211> LENGTH: 17
<212> TYPE: DNA
<213> ORGANISM: Artificial Sequence
<220> FEATURE:
<223> OTHER INFORMATION: 16s rDNA fusion primer_518R

<400> SEQUENCE: 2
wttaccgcgg ctgctgg                                                  17

The invention claimed is:

1. A method of treating an inflammatory disease comprising:
  administering a pharmaceutical composition comprising an active ingredient of *Lactobacillus plantarum* derived extracellular vesicles to a subject in need thereof,
  wherein the composition does not contain the cells of *Lactobacillus plantarum*, and the inflammatory disease is selected from the group consisting of atopic dermatitis, chronic rhinitis, chronic rhinosinusitis, asthma, chronic obstructive pulmonary disease (COPD), and sepsis.

* * * * *